United States Patent
Handique et al.

(10) Patent No.: US 11,052,396 B2
(45) Date of Patent: *Jul. 6, 2021

(54) SYSTEM AND METHOD FOR ISOLATING AND ANALYZING CELLS

(71) Applicant: Bio-Rad Laboratories, Inc., Hercules, CA (US)

(72) Inventors: Kalyan Handique, Ann Arbor, MI (US); Priyadarshini Gogoi, Ann Arbor, MI (US); Saedeh Javdani Sepehri, Ypsilanti, MI (US); Kyle Gleason, Brighton, MI (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,416

(22) Filed: Nov. 4, 2019

(65) Prior Publication Data

US 2020/0061619 A1 Feb. 27, 2020

Related U.S. Application Data

(63) Continuation of application No. 16/049,173, filed on Jul. 30, 2018, now Pat. No. 10,512,914, which is a continuation of application No. 15/442,222, filed on Feb. 24, 2017, now Pat. No. 10,391,490, which is a continuation-in-part of application No. 14/289,155, filed on May 28, 2014, now Pat. No. 9,856,535.

(60) Provisional application No. 61/829,537, filed on May 31, 2013, provisional application No. 62/299,427, filed on Feb. 24, 2016, provisional application No. 62/423,322, filed on Nov. 17, 2016.

(51) Int. Cl.
| | |
|---|---|
| *B01L 3/00* | (2006.01) |
| *G01N 15/10* | (2006.01) |
| *G01N 15/14* | (2006.01) |
| *C12M 1/00* | (2006.01) |
| *C12Q 1/6834* | (2018.01) |
| *C12Q 1/6841* | (2018.01) |
| *G01N 33/574* | (2006.01) |
| *G01N 15/00* | (2006.01) |

(52) U.S. Cl.
CPC ....... *B01L 3/502761* (2013.01); *C12M 47/04* (2013.01); *C12Q 1/6834* (2013.01); *C12Q 1/6841* (2013.01); *G01N 15/1056* (2013.01); *G01N 15/1434* (2013.01); *G01N 15/1484* (2013.01); *G01N 33/57415* (2013.01); *G01N 33/57423* (2013.01); *B01L 2200/027* (2013.01); *B01L 2200/0668* (2013.01); *B01L 2200/16* (2013.01); *B01L 2300/087* (2013.01); *B01L 2300/0819* (2013.01); *B01L 2300/0867* (2013.01); *B01L 2300/1827* (2013.01); *B01L 2400/0406* (2013.01); *B01L 2400/0445* (2013.01); *B01L 2400/0487* (2013.01); *B01L 2400/086* (2013.01); *C12Q 2565/518* (2013.01); *G01N 2015/0065* (2013.01); *G01N 2800/52* (2013.01)

(58) Field of Classification Search
CPC ................................ B01L 3/502761
USPC ........................................... 435/287
See application file for complete search history.

(56) References Cited

U.S. PATENT DOCUMENTS

| | | | |
|---|---|---|---|
| 4,475,411 | A | 10/1984 | Wellerfors |
| 4,551,435 | A | 11/1985 | Liberti et al. |
| 4,710,635 | A | 12/1987 | Chupp |
| 5,266,269 | A | 11/1993 | Niiyama et al. |
| 5,281,540 | A | 1/1994 | Merkh et al. |
| 5,491,343 | A | 2/1996 | Brooker |
| 5,541,064 | A | 7/1996 | Bacus et al. |
| 5,547,849 | A | 8/1996 | Baer et al. |
| 5,851,488 | A | 12/1998 | Saul et al. |
| 5,883,370 | A | 3/1999 | Walker et al. |
| 5,888,370 | A | 3/1999 | Becker et al. |
| 5,993,630 | A | 11/1999 | Becker et al. |
| 5,993,632 | A | 11/1999 | Becker et al. |
| 6,016,712 | A | 1/2000 | Warden et al. |
| 6,127,177 | A | 10/2000 | Toner et al. |
| 6,133,030 | A | 10/2000 | Bhatia et al. |
| 6,150,180 | A | 11/2000 | Parce et al. |
| 6,174,683 | B1 | 1/2001 | Hahn |
| 6,221,663 | B1 | 4/2001 | Bhatia et al. |
| 6,228,624 | B1 | 5/2001 | Terstappen |
| 6,281,008 | B1 | 8/2001 | Komai et al. |
| 6,287,832 | B1 | 9/2001 | Becker et al. |
| 6,365,362 | B1 | 4/2002 | Terstappen et al. |
| 6,410,724 | B1 | 6/2002 | Dejean et al. |
| 6,433,134 | B1 | 8/2002 | Patron et al. |
| 6,525,997 | B1 | 2/2003 | Narayanaswami et al. |
| 6,563,634 | B2 | 5/2003 | Shimada et al. |
| 6,613,525 | B2 | 9/2003 | Nelson et al. |
| 6,623,983 | B1 | 9/2003 | Terstappen et al. |
| 6,641,708 | B1 | 11/2003 | Becker et al. |
| 6,645,731 | B2 | 11/2003 | Terstappen et al. |

(Continued)

FOREIGN PATENT DOCUMENTS

| | | |
|---|---|---|
| EP | 2414548 A2 | 2/2012 |
| EP | 2414548 B1 | 10/2015 |

(Continued)

OTHER PUBLICATIONS

International Search Report and Written Opinion for application No. PCT/US20/31502 dated Sep. 16, 2020.

(Continued)

*Primary Examiner* — Karla A Dines
(74) *Attorney, Agent, or Firm* — Jeffrey Schox

(57) ABSTRACT

A system and method for isolating and analyzing single cells, comprising: a substrate having a broad surface; a set of wells defined at the broad surface of the substrate, and a set of channels, defined by the wall, that fluidly couple each well to at least one adjacent well in the set of wells; and fluid delivery module defining an inlet and comprising a plate, removably coupled to the substrate, the plate defining a recessed region fluidly connected to the inlet and facing the broad surface of the substrate, the fluid delivery module comprising a cell capture mode.

20 Claims, 17 Drawing Sheets

(56) References Cited

U.S. PATENT DOCUMENTS

| | | |
|---|---|---|
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,866,823 B2 | 3/2005 | Wardlaw |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,211,301 B2 | 7/2012 | Safar et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,746,413 B2 | 8/2017 | Handique et al. |
| 9,752,181 B2 | 9/2017 | Handique et al. |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 10,376,889 B1 | 8/2019 | Masquelier et al. |
| 10,401,373 B1 | 9/2019 | Holmes et al. |
| 10,408,736 B1 | 9/2019 | Handique |
| 10,533,152 B1 | 1/2020 | Belgrader et al. |
| 10,718,007 B2 | 7/2020 | Handique et al. |
| 2002/0009759 A1 | 1/2002 | Terstappen et al. |
| 2002/0028431 A1 | 3/2002 | Julien |
| 2002/0036142 A1 | 3/2002 | Gascoyne et al. |
| 2002/0036823 A1 | 3/2002 | Shimada et al. |
| 2002/0098535 A1 | 7/2002 | Wang et al. |
| 2002/0109838 A1 | 8/2002 | Columbus |
| 2002/0119482 A1 | 8/2002 | Nelson et al. |
| 2002/0192808 A1 | 12/2002 | Gambini et al. |
| 2003/0129676 A1 | 7/2003 | Terstappen et al. |
| 2003/0138941 A1 | 7/2003 | Gong et al. |
| 2004/0029241 A1 | 2/2004 | Hahn et al. |
| 2004/0106130 A1 | 6/2004 | Besemer et al. |
| 2004/0160599 A1 | 8/2004 | Hamamatsu et al. |
| 2004/0191891 A1 | 9/2004 | Tsinberg et al. |
| 2004/0218472 A1 | 11/2004 | Narayanaswami et al. |
| 2004/0229349 A1 | 11/2004 | Daridon |
| 2004/0248318 A1 | 12/2004 | Weinberger et al. |
| 2005/0001176 A1 | 1/2005 | Loney et al. |
| 2005/0014201 A1 | 1/2005 | Deuthsch |
| 2005/0037343 A1 | 2/2005 | Fagnani et al. |
| 2005/0042685 A1 | 2/2005 | Albert et al. |
| 2005/0063863 A1 | 3/2005 | Columbus |
| 2005/0112589 A1 | 5/2005 | Hahn et al. |
| 2005/0118640 A1 | 6/2005 | Kureshy et al. |
| 2005/0123445 A1 | 6/2005 | Blecka et al. |
| 2005/0158804 A1 | 7/2005 | Yao et al. |
| 2005/0164236 A1 | 7/2005 | Su et al. |
| 2005/0181463 A1 | 8/2005 | Rao et al. |
| 2005/0265815 A1 | 12/2005 | Rodi |
| 2006/0040274 A1 | 2/2006 | Tsinberg |
| 2006/0040407 A1 | 2/2006 | Falcovitz-Gerassi et al. |
| 2006/0050142 A1 | 3/2006 | Scott et al. |
| 2006/0115380 A1 | 6/2006 | Kagan et al. |
| 2006/0128006 A1 | 6/2006 | Gerhardt et al. |
| 2006/0141045 A1 | 6/2006 | Bhatt et al. |
| 2006/0147959 A1 | 7/2006 | Bell et al. |
| 2006/0160243 A1 | 7/2006 | Tang et al. |
| 2006/0257992 A1 | 11/2006 | McDevitt et al. |

(56) References Cited

U.S. PATENT DOCUMENTS

| | | |
|---|---|---|
| 2006/0263250 A1 | 11/2006 | Blouin et al. |
| 2007/0026381 A1 | 2/2007 | Huang et al. |
| 2007/0111302 A1 | 5/2007 | Handique et al. |
| 2007/0154960 A1 | 7/2007 | Connelly et al. |
| 2007/0161051 A1 | 7/2007 | Tsinberg et al. |
| 2007/0172903 A1 | 7/2007 | Toner et al. |
| 2007/0238089 A1 | 10/2007 | Rosenthal et al. |
| 2007/0243523 A1 | 10/2007 | Ionescu-Zanetti et al. |
| 2007/0252265 A1 | 11/2007 | Sander |
| 2007/0264675 A1 | 11/2007 | Toner et al. |
| 2007/0264705 A1 | 11/2007 | Dodgson |
| 2007/0275418 A1 | 11/2007 | Hollmann et al. |
| 2008/0003224 A1 | 1/2008 | Fong et al. |
| 2008/0014589 A1 | 1/2008 | Link et al. |
| 2008/0068588 A1 | 3/2008 | Hess et al. |
| 2008/0090239 A1 | 4/2008 | Shoemaker et al. |
| 2008/0096212 A1 | 4/2008 | Bell et al. |
| 2008/0113358 A1 | 5/2008 | Kapur et al. |
| 2008/0113906 A1 | 5/2008 | Ding et al. |
| 2008/0124726 A1 | 5/2008 | Monforte |
| 2008/0182273 A1 | 7/2008 | Hansen et al. |
| 2008/0206751 A1 | 8/2008 | Squirrell et al. |
| 2008/0207615 A1 | 8/2008 | Bell et al. |
| 2008/0220422 A1 | 9/2008 | Shoemaker et al. |
| 2008/0234264 A1 | 9/2008 | Bell et al. |
| 2008/0240539 A1 | 10/2008 | George et al. |
| 2008/0257735 A1 | 10/2008 | Jeon et al. |
| 2008/0317325 A1 | 12/2008 | Ortyn et al. |
| 2009/0014360 A1 | 1/2009 | Toner et al. |
| 2009/0061450 A1 | 3/2009 | Hunter |
| 2009/0081773 A1 | 3/2009 | Kaufman |
| 2009/0141593 A1 | 6/2009 | Taha |
| 2009/0153844 A1 | 6/2009 | Peter et al. |
| 2009/0162853 A1 | 6/2009 | Clark et al. |
| 2009/0215088 A1 | 8/2009 | Forsyth et al. |
| 2009/0220979 A1 | 9/2009 | Davis et al. |
| 2009/0258383 A1 | 10/2009 | Kovac et al. |
| 2009/0317836 A1 | 12/2009 | Kuhn et al. |
| 2010/0120077 A1 | 5/2010 | Daridon |
| 2010/0127168 A1 | 5/2010 | Khursheed |
| 2010/0210009 A1 | 8/2010 | Willson et al. |
| 2010/0227387 A1 | 9/2010 | Safar et al. |
| 2010/0232675 A1 | 9/2010 | Ortyn et al. |
| 2010/0233693 A1 | 9/2010 | Kopf-Sill et al. |
| 2010/0261179 A1 | 10/2010 | Betley et al. |
| 2010/0291584 A1 | 11/2010 | Tseng et al. |
| 2010/0304485 A1 | 12/2010 | Karnik et al. |
| 2010/0304978 A1 | 12/2010 | Robbins et al. |
| 2011/0003380 A1 | 1/2011 | Miltenyi et al. |
| 2011/0045994 A1 | 2/2011 | Voldman et al. |
| 2011/0053151 A1 | 3/2011 | Hansen et al. |
| 2011/0104718 A1 | 5/2011 | Rao et al. |
| 2011/0117634 A1 | 5/2011 | Halamish et al. |
| 2011/0143964 A1 | 6/2011 | Zhou et al. |
| 2011/0227558 A1 | 9/2011 | Mannion et al. |
| 2011/0236904 A1 | 9/2011 | Hauch et al. |
| 2011/0280467 A1 | 11/2011 | George et al. |
| 2012/0021456 A1 | 1/2012 | Levine et al. |
| 2012/0071355 A9 | 3/2012 | Cooney |
| 2012/0071643 A1 | 3/2012 | Helfer et al. |
| 2012/0129190 A1 | 5/2012 | Chiu et al. |
| 2012/0156675 A1 | 6/2012 | Lueerssen et al. |
| 2012/0164679 A1 | 6/2012 | Vrouwe et al. |
| 2012/0194805 A1 | 8/2012 | Ness et al. |
| 2013/0116102 A1 | 5/2013 | Hansen |
| 2013/0130376 A1 | 5/2013 | Serobyan et al. |
| 2013/0171628 A1 | 7/2013 | Di et al. |
| 2013/0230860 A1 | 9/2013 | Park et al. |
| 2013/0244906 A1 | 9/2013 | Collins |
| 2013/0259635 A1 | 10/2013 | Maslana et al. |
| 2014/0173443 A1 | 6/2014 | Hawkins et al. |
| 2014/0212881 A1 | 7/2014 | Handique et al. |
| 2014/0213487 A1 | 7/2014 | Freudenthal et al. |
| 2014/0272965 A1 | 9/2014 | Handique et al. |
| 2014/0315237 A1 | 10/2014 | Masujima et al. |
| 2014/0357511 A1 | 12/2014 | Handique et al. |
| 2014/0370612 A1 | 12/2014 | Bassler et al. |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0160135 A1 | 6/2015 | Tibbe et al. |
| 2015/0160931 A1 | 6/2015 | Glazer et al. |
| 2015/0204864 A1 | 7/2015 | Fan et al. |
| 2015/0299784 A1 | 10/2015 | Fan et al. |
| 2015/0376609 A1 | 12/2015 | Hindson et al. |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0199838 A1 | 7/2016 | Handique et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2016/0367991 A1 | 12/2016 | Petersen et al. |
| 2017/0044525 A1 | 2/2017 | Kaper et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |
| 2019/0002814 A1 | 1/2019 | Masquelier et al. |

FOREIGN PATENT DOCUMENTS

| | | |
|---|---|---|
| JP | 2006098696 A | 4/2006 |
| JP | 2008136415 A | 6/2008 |
| WO | 2003035909 A2 | 5/2003 |
| WO | 2006098696 A1 | 9/2006 |
| WO | 2010120818 A2 | 10/2010 |
| WO | 2015133337 A1 | 9/2015 |
| WO | 2018013723 A1 | 1/2018 |
| WO | 2018058073 A2 | 3/2018 |

OTHER PUBLICATIONS

International Search Report and Written Opinion for PCT Application No. PCT/US17/62099 dated Feb. 12, 2018.

Seale, K. T. et al. "Mirrored pyramidal wells for simultaneous multiple vantage point microscopy." Journal of Microscopy (2008) 232 1-6. (Year: 2008).

Sugio et al. (Sensors and Actuators, B99, 2004, pp. 156-162).

Supplemental information from Tan et al. PNAS (2007) 104. (Year: 2007).

Tan, Wei-Heang et al. "A trap-and-release integrated microfluidic system for dynamic microarray applications." PNAS (2007) 104 1146-1151. (Year: 2007).

"Guo, P. et al. Microfluidic capture and release of bacteria in a conical nanopore array. Lab Chip. vol. 12, p. 558-561, 2012, published online Nov. 2011.", Jun. 23, 2017 00:00:00.0.

"International Preliminary Report on Patentability for OCT Application No. PCT/US17/62099 dated May 31, 2019."

"Lindstrom, Sara (Royal Institute of Technology, Stockholm, Sweden, 2009, pp. 1-80)".

Australian Examination Report for Application No. 2018323449, dated Feb. 25, 2020.

European Search Report for application No. 17870743 dated May 26, 2020.

(56) References Cited

OTHER PUBLICATIONS

International Search Report for PCT Application No. PCT/US2018/048353 dated Nov. 5, 2018.

Planar Broad Surface

Non-Planar Broad Surface

Non-Planar Broad Surface

SYSTEM AND METHOD FOR ISOLATING AND ANALYZING CELLS

CROSS-REFERENCE TO RELATED APPLICATIONS

This application is a continuation of U.S. application Ser. No. 16/049,173, filed 30 Jul. 2018, which is a continuation of U.S. application Ser. No. 15/442,222, filed 24 Feb. 2017, which is a continuation-in-part of U.S. application Ser. No. 14/289,155 filed 28 May 2014, which claims the benefit of U.S. Provisional Application No. 61/829,537, filed 31 May 2013, all of which are incorporated in their entirety by this reference. U.S. application Ser. No. 15/442,222, filed 24 Feb. 2017, also claims the benefit of U.S. Provisional Application No. 62/299,427 filed on 24 Feb. 2016, as well as U.S. Provisional Application No. 62/423,322 filed on 17 Nov. 2016, which are each incorporated in their entirety by this reference.

TECHNICAL FIELD

This invention relates generally to the cell sorting field, and more specifically to a new and useful system and method for isolating and analyzing cells within the cell sorting field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems suffer from various shortcomings that prevent widespread adoption for cell-specific testing. For example, flow cytometry requires that the cell be simultaneously identified and sorted, and limits cell observation to the point at which the cell is sorted. Flow cytometry fails to allow for multiple analyses of the same cell within a single flow cytometry workflow, and does not permit arbitrary cell subpopulation sorting. Conventional microfluidic devices rely on cell-specific antibodies for cell selection, wherein the antibodies that are bound to the microfluidic device substrate selectively bind to cells expressing the desired antigen. Conventional microfluidic devices can also fail to allow for subsequent cell removal without cell damage, and only capture the cells expressing the specific antigen; non-expressing cells, which could also be desired, are not captured by these systems. Such loss of cell viability can preclude live-cell assays from being performed on sorted or isolated cells. Cellular filters can separate sample components based on size without significant cell damage, but suffer from clogging and do not allow for specific cell identification, isolation of individual cells, and retrieval of identified individual cells. Other technologies in this field are further limited in their ability to allow multiplex assays to be performed on individual cells, while minimizing sample preparation steps and overly expensive instrumentation.

Thus, there is a need in the cell sorting field to create new and useful systems and methods for isolating and analyzing cells, and the inventions disclosed herein provide such useful systems and methods.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
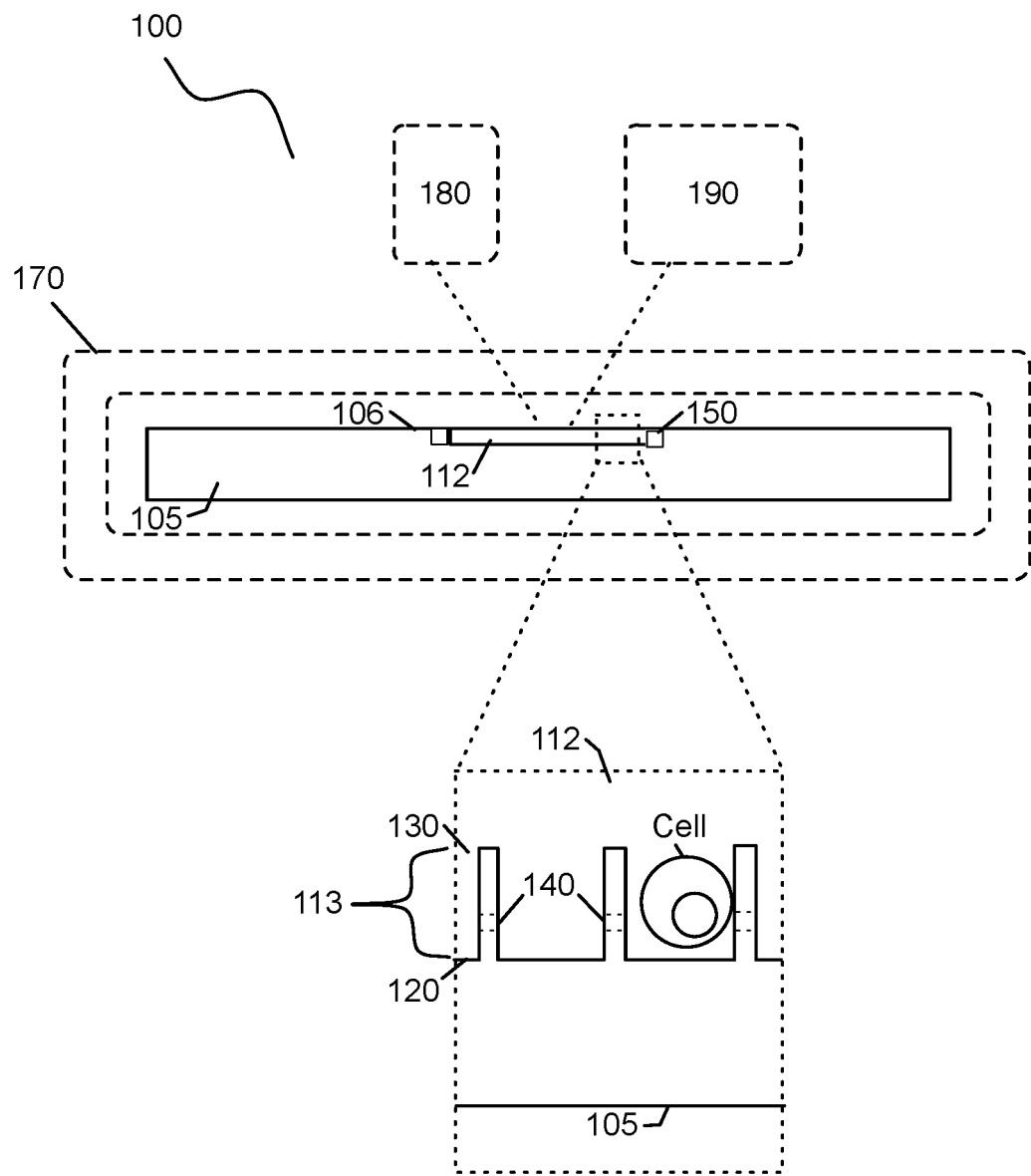
FIG. 1 is a schematic representation of an embodiment of a system for isolating and analyzing cells.

As shown in FIG. 1, a system 100 for isolating and analyzing a set of cells comprises: a substrate 105 having a broad surface; a set of wells 112 defined at the broad surface of the substrate, each well 113 in the set of wells 112 including a base surface 120 defined within the substrate, an open surface 130 directly opposing the base surface 120, a wall 116 extending between the base surface 120 and the open surface 130 and defining a set of channels 140 that fluidly couple each well to at least one adjacent well in the set of wells. The set of wells 112 can be arranged in an array no, or in any other suitable arrangement. In some variations, the system 100 can further include a perimeter channel 150 surrounding the set of wells 112 and fluidly coupled to each well in an exterior subset 115 of the set of wells by way of at least one channel in the set of channels of each well in the exterior subset of the set of wells. To facilitate sample or fluid delivery to the set of wells 112, the system 100 can further include a fluid delivery module 170 configured to couple to the substrate 105 and transfer a sample containing the set of cells and/or another fluid to the set of wells 112. To facilitate cell extraction from the set of wells once isolated, the system 100 can include a cell removal module 180 that extracts at least one of a single cell and a cell cluster from a well of the set. Additionally or alternatively, the system 100 can include an encapsulation module 190 configured to encapsulate the set of cells at the set of wells 112, and facilitate delivery of reagents to encapsulated cells of the set of cells at the set of wells 112. Additionally or alternatively, the system 100 can include an imaging subsystem 195 configured to optically image the contents of the set of wells 112, and enable identification of cells retained by wells off the set of wells 112. Additionally or alternatively, the system 100 can include a flow control subsystem 199 configured to control fluid and/or sample flow through the system 100, as well as reagent flow or any other suitable flow through the system requiring control and/or actuation. Additionally or alternatively, the system 100 can include a thermal control module for controlling the temperature of portions of the system 100.

The system 100 functions to isolate, capture, retain, and analyze cells of a cell population, in at least one of single-cell format and single-cluster format, at known, addressable locations, and further to facilitate performance of multiple single-cell assays that can be performed on individual cells (e.g., rare cells in a biological sample) or clusters of cells (e.g., doublets, triplets). Once cells are captured in defined locations determined by single cell capture wells, a fluidic network of the system 100 can be used to provide and deliver reagents simultaneously, sequentially, and/or in repetition to enable a variety of cellular, sub-cellular or molecular reactions to be performed in each of the single cells/cell clusters. Alternatively, the system 100 can function to capture and process non-cell particles (e.g., nucleic acid material, other biological material, other non-biological material, etc.). The system 100 can also allow optical interrogation and detection of events on each of the captured cells at a single cell/single cluster level. The system 100 can additionally or alternatively enable selective release and/or selective removal of one or more of the captured cells for further processing and analysis. In some embodiments, the system 100 can confer the benefits of real-time cell tracking, viable cell retrieval, and selective downstream molecular analysis (e.g., electrophoresis), either in the same microfluidic chip or off-chip. In some embodiments, the system 100 can be used to capture circulating tumor cells (CTCs) and subpopulations of CTCs, such as circulating stem cells (CSCs), but can additionally or alternatively be used to capture any other suitable cell of possible interest. The system 100 is preferably defined on a substrate, more preferably a microfluidic chip, but can alternatively be located on or defined by any suitable substrate.

In specific examples, the system 100 can be used with method(s) operable for single cell polymerase chain reaction (PCR), wherein such systems can facilitate high efficiency capture of cells (e.g., 1000 s of cells, 10,000 s of cells, 10,000 s of cells, etc.) in single cell format (or single cluster format) within wells, as well as on-chip reagent delivery to the wells, incubation, and thermocycling in order to provide a cell-to-PCR workflow. In more detail, microfluidic and other portions of the system can be operable to perform assays (e.g., assays associated with ARV7 mRNA) using PCR with samples (e.g., prostate clinical samples) with single cell or single cell cluster resolution. In specific examples, the system 100 can accommodate sample volumes on the order to 1 mL within a reservoir associated with particle capture wells, thereby providing the ability to process larger sample volumes.

Figure 13:
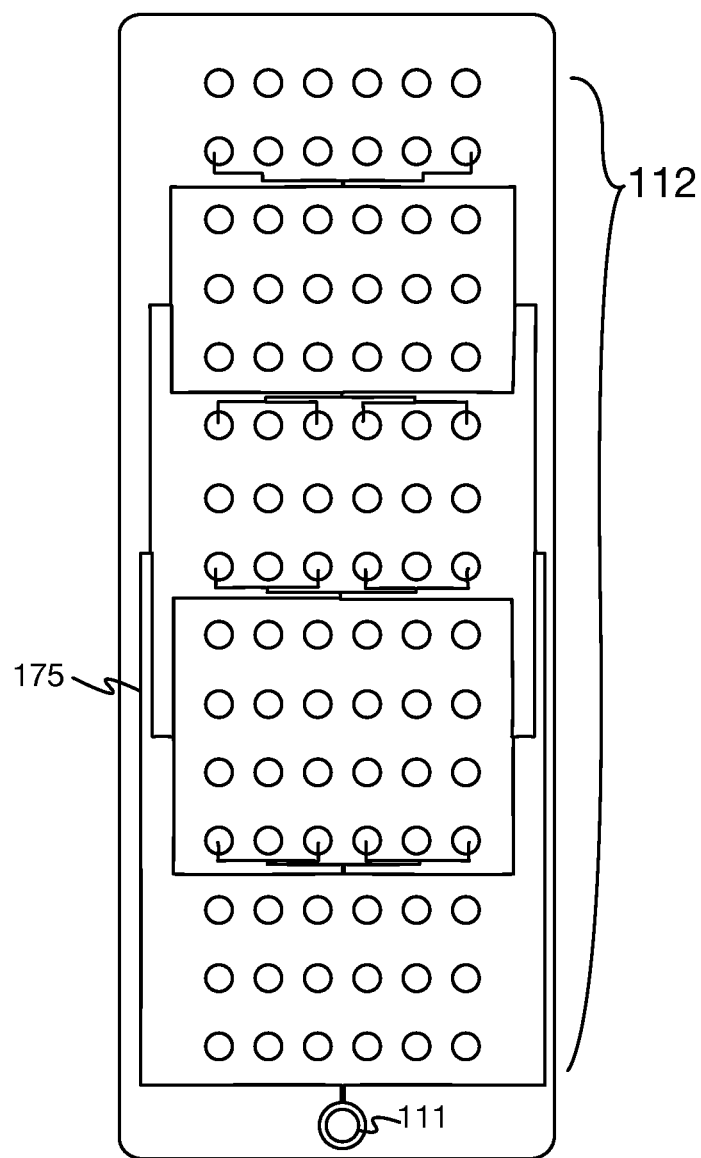
FIG. 13 depicts an example configuration of a portion of a system for isolating and analyzing cells.

The system 100 preferably achieves individual cell capture and retention from a biological sample including a cell population, without antibody coated wells, and preferably maintains the viability of the cells throughout isolation, capture, retention, and/or removal. Individual cell capture is preferably achieved by flowing a sample containing a group of single cells within a fluid layer over the set of wells 112 in a direction parallel (e.g., substantially parallel, within 0.1 degrees of parallel, within 1 degree of parallel, within 45 degrees of parallel, completely parallel, etc.) to the broad surface of the substrate, and capturing the cells once they have descended through the fluid layer towards the set of wells 112 under the influence of gravity. Alternatively, individual cell capture can be achieved by delivering a sample containing a group of single cells into a fluid layer provided by a reservoir, over the set of wells 112 in a direction perpendicular to the broad surface of the substrate, and capturing the cells once they have descended through the fluid layer towards the set of wells 112 under the influence of gravity. However, in some variations, individual cell capture can additionally or alternatively be achieved by any suitable mechanism for promoting single cell transfer into a well of the set of wells. Furthermore, the system 100 is preferably configured to prevent undesired fluid currents that can lift cells from the substrate or move cells/cell clusters from wells at which the cells were initially captured. However, in some variations, the system 100 can be configured to facilitate moving of cells/cell clusters in any suitable manner. The flow path of a fluid (e.g., biological sample, process reagent) through the system 100 is preferably multi-directional and uniform, such that each cell/cell cluster in the system 100 experiences consistent conditions (e.g., gradient length scales along the flow path of flow properties such as pressure, density, temperature, solution composition, and other suitable properties are large relative to the length scales of the system); however, the flow path can alternatively be unidirectional, bi-directional, or have any other suitable characteristic(s). In a specific example, as shown in FIG. 13, the flow path of a fluid through the system is defined by a set of fluid pathways of equal length (e.g., substantially equal length, equal length to within manufacturability tolerances, etc.) that are configured such that a reagent supplied at a common inlet to the set of fluid pathways arrives at each end point (e.g., a single well) at substantially the same time point (e.g., at the same time, within 1 second, within 1 minute, etc.). Cell transport, isolation, sorting and viability maintenance can additionally be accomplished by controlling the sample flow rate through the system (e.g., by adjusting the flow rate so that a characteristic length scale of the flow is of a similar order as a characteristic length scale of a well, by dithering the flow rate between high and low flow conditions, etc.), or through any other suitable means.

In operation, the system 100 preferably receives a biological sample including the cell population and facilitates distribution of the biological sample uniformly across the set of wells 112 (e.g., using uniform cross flow, smearing, a cytospin procedure, etc.). However, the system 100 can additionally or alternatively facilitate distribution of the biological sample across the set of wells using positive pressure (e.g., positive pressure at an inlet to the array)

and/or negative pressure (e.g., negative pressure at an outlet of the array). Additionally or alternatively, actuation pressure that facilitates sample distribution can be cycled in a pulse-width modulation fashion or sinusoidal fashion to provide net actuation pressure, either net positive at the inlet or net negative at the outlet. As such, desired cells having a defining characteristic (e.g., size-based characteristic, density-based characteristic, adhesion-based characteristic, etc.) can be trapped within a well 113 as the biological sample flows across the set of wells 112. For example, in the variation of the system 100 configured to capture CTCs, the wells 113 are preferably configured based upon defining morphological features of CTC cells, in order to facilitate capture and retention of CTCs in single cell or single cluster format. However, the system 100 can additionally or alternatively be configured to retain and facilitate processing or any other suitable particle of interest in any other suitable format. Actuation pressure is preferably provided by the flow control subsystem 199 (e.g., a manually-operated pipette, automated fluid-handling robot, electromechanical micropump, etc.) in fluid communication with the system 100, but can alternatively or additionally be provided by any suitable mechanism.

1.1 System—Substrate

The substrate 105 has a broad surface 106, and functions to provide a medium at which the set of wells 112 can be defined. The substrate 105 is preferably composed of a rigid material with high transparency (e.g., a transparent material, a translucent material), in order to facilitate imaging of the substrate 105 to analyze captured single cells/cell clusters. The high transparency material is preferably optically transparent, but can additionally or alternatively be transparent and/or translucent to other portions of the electromagnetic spectrum (e.g., microwaves, near infra-red, ultraviolet, etc.) In a few such variations, the substrate 105 can be composed of any one or more of: glass, a silicone-based material, a polymer, and any other suitable material with high transparency. Alternatively, the substrate 105 can be composed of any other suitable material having any other suitable optical properties. In a few such variations, the substrate can be composed of any one or more of: a ceramic material, a semi-conducting material, a polymer, and any other suitable material. The substrate 105 composition can be configured to provide desired characteristics relating to any one or more of: mechanical characteristics (e.g., substrate mechanical properties as a mechanical stimulus), optical properties (e.g., transparency), electrical properties (e.g., conductivity), thermal properties (e.g., conductivity, specific heat, etc.), physical characteristics (e.g., wettability, porosity, etc.), and any other suitable characteristic. The substrate 105 can be processed using any one or more of: etching methods, molding methods, printing methods (e.g., 3D printing processes), machining methods, and any other suitable manufacturing processes suited to a brittle, elastic, or ductile substrate material.

Figure 2A:
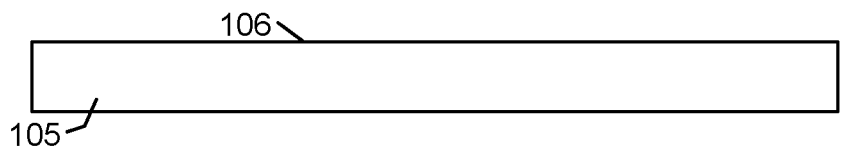
FIGS. 2A-2C depict variations of a portion of a system for isolating and analyzing cells.
Figure 2B:
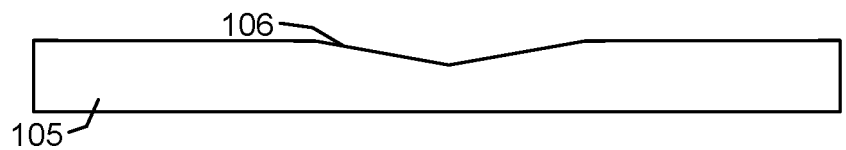
Figure 2C:

The broad surface 106 of the substrate 105 is preferably a planar surface, such that microfluidic elements of the system 100 are defined at least partially at a planar surface. Alternatively, the broad surface 106 of the substrate 105 can be a non-planar surface, as shown in FIG. 2A-2C, such that microfluidic elements of the system 100 are defined at least partially at a non-planar surface. In variations, the non-planar surface can be a concave surface, a convex surface, or a surface having concave, planar, and/or convex surfaces. Such variations can facilitate various methods of depositing and distributing a sample at the set of wells 112. In any variations of the substrate 105 including a non-planar broad surface 106, the non-planar portion(s) are preferably shallow (e.g., having a small depth relative to a width of the broad surface) or short (e.g., having a small height relative to a width of the broad surface); however, the non-planar portion(s) can additionally or alternatively include portions that are deep (e.g., having a large depth relative to a width of the broad surface) or tall (e.g., having a large height relative to a width of the broad surface). In examples of a concave surface, the concave surface can be any one or more of: a semi-spherical surface, a semi-cylindrical surface, a parabolic surface, a pyramidal surface, a conical surface, an ogive surface, a semi-ellipsoidal surface, and any other suitable surface. In examples of a convex surface, the convex surface can be any one or more of: semi-spherical surface, a semi-cylindrical surface, a parabolic surface, a pyramidal surface, a conical surface, an ogive surface, a semi-elliopsoidal surface, and any other suitable surface. In variations of the substrate 105 including a non-planar broad surface 106, the non-planar broad surface 106 preferably has a rotational axis of symmetry, for instance, to facilitate sample distribution by a cytospinning process. However, the surface can alternatively have any other suitable axis or type of symmetry, or can be asymmetrical. In any of these variations, the non-planar surface of the broad surface 106 can be produced by any one or more of: molding, by polishing, by spinning a material in a flow phase followed by setting the material, by machining, by printing (e.g., 3D printing), by etching, and by any other suitable process.

In a specific example, the set of wells 112 is defined within a silicon mold using a three mask photolithographic process and deep reactive ion etching (DRIE) process to etch microfluidic elements into the silicon mold. In the specific example, the etched elements of the silicon mold are then transferred polymethylmethacrylate (PMMA) sheets as a substrate 105 using a hot embossing process. The substrate 105 in the specific example has dimensions of 3 inches by 1 inch, in order to substantially match dimensions of a glass microscope slide. In variations of the specific example, and/or for other variations of the set of wells 112, hot embossing of cyclic olefin polymer (COP) can be substituted for PMMA to form the microfluidic structures of the set of wells 112. However, the substrate 105 can alternatively be any other suitable substrate 120 processed in any other suitable manner.

1.2 System—Set of Wells

The set of wells 112 functions to capture the set of cells in addressable, known locations such that the set of cells can be individually identified, processed, and analyzed. As such, the set of wells 112 is preferably configured to facilitate cell capture in at least one of a single-cell format and single-cluster format. As shown in FIG. 1, the set of wells 112 is preferably defined at the broad surface 106 of the substrate 105, each well 113 in the set of wells 112 including a base surface 120 defined within the substrate, an open surface 130 directly opposing the base surface 120, and a set of channels 140 that fluidly couple each well to at least one adjacent well in the set of wells 112. There are preferably at least 250,000 wells in the set of wells; however, there can be any suitable number of wells (e.g., 100, 1000, 1 million, etc.).

Figure 20A:
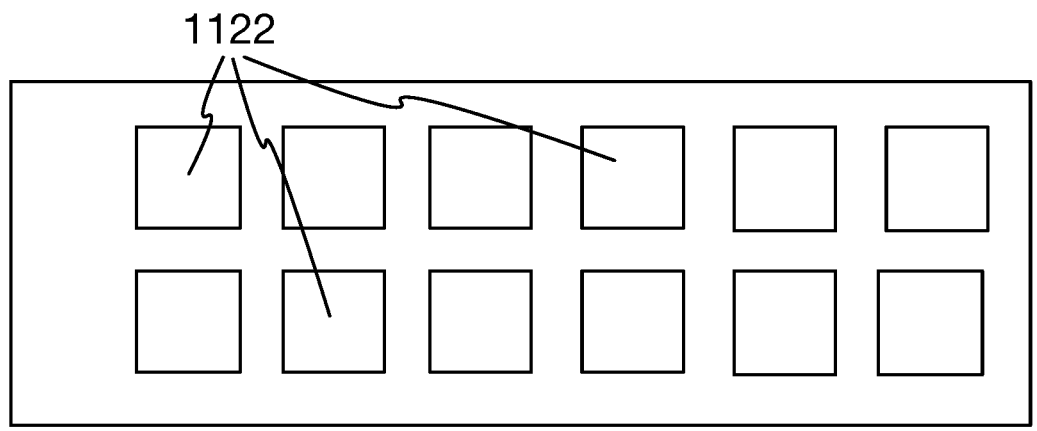
FIGS. 20A-B depict a schematic diagram of two variations of a portion of a system for isolating and analyzing cells.
Figure 20B:
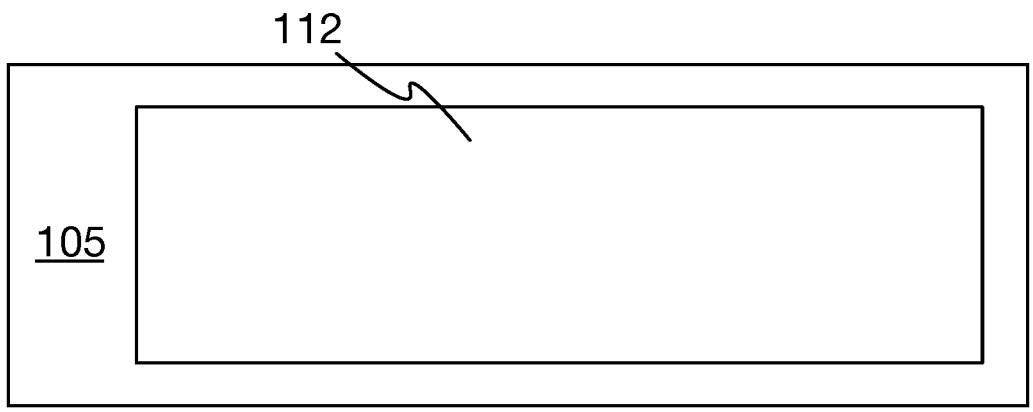

In variations including subsets of wells, the subsets can be separated from one another. In a first variation, each subset can be separated from other subsets by a portion of the substrate in which no wells are defined (e.g., a flat region of the broad surface). In a second variation, the subsets can be fluidically-isolated regions of a contiguous arrangement of wells, in which none of the wells of a particular subset are fluidly coupled to a well of another subset. In a specific example, as shown in FIG. 20A, the substrate defines twelve distinct subsets 1122 of the set of wells 112, arranged in a two-by-six grid, that are separated from adjacent subsets by flat region of the broad surface, with a uniform spacing (e.g., 1 mm, 100 microns, 3 mm, etc.) between array edges. The subsets of wells can be further divided into groups (e.g., groups of seven wells within a subset of 20,000 wells of a 250,000 well set of wells), and any suitable interconnectivity between wells (e.g., among subsets, between groups, etc.) can be provided by the set of channels of each well. Such configurations may permit efficient cell capture (e.g., by a group including seven interconnected wells) by groups of wells, while allowing the set of wells to be exposed to multiple distinct samples (e.g., one sample per subset of the set of wells). An example of such subdivision of wells is shown in FIGS. 18 and 21A-21C, with wells approximately 30 microns in diameter, 30 microns deep, and wall thicknesses of 4-5 microns (e.g., which provides more efficient cell capture). However, in related variations, the set of wells 112 can alternatively be subdivided and/or interconnected in any suitable manner. The subsets and/or groups of wells can be arranged in any suitable manner. For example, the subsets can be arranged in a rectilinear fashion (e.g, a grid layout of well subsets) and the groups can be arranged in a packed configuration (e.g., hexagonal close-packed, square lattice, etc.), and vice versa; the arrangement of the groups and subsets are preferably independent of one another, but can alternatively be based on one another (e.g., the subsets are arranged in a rectilinear fashion because the groups are arranged in a rectilinear fashion).

Figure 21A:
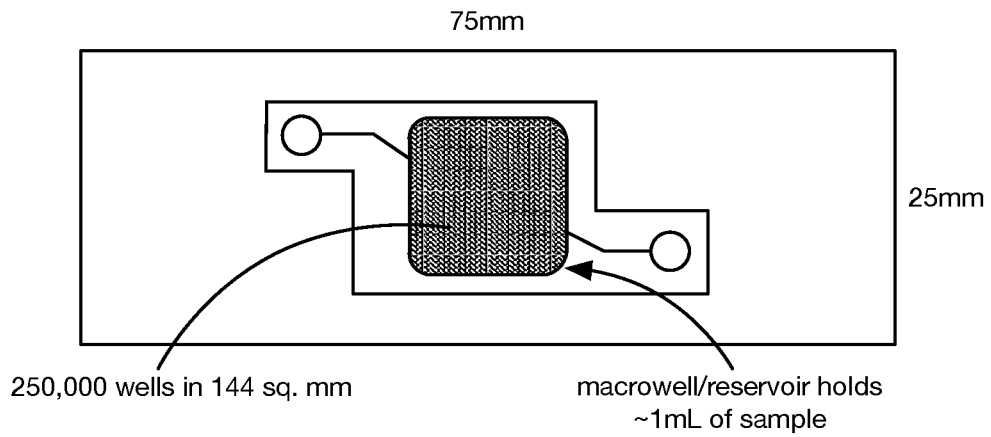
FIGS. 21A-C depict examples of an embodiment of a system for isolating and analyzing cells.
Figure 21B:
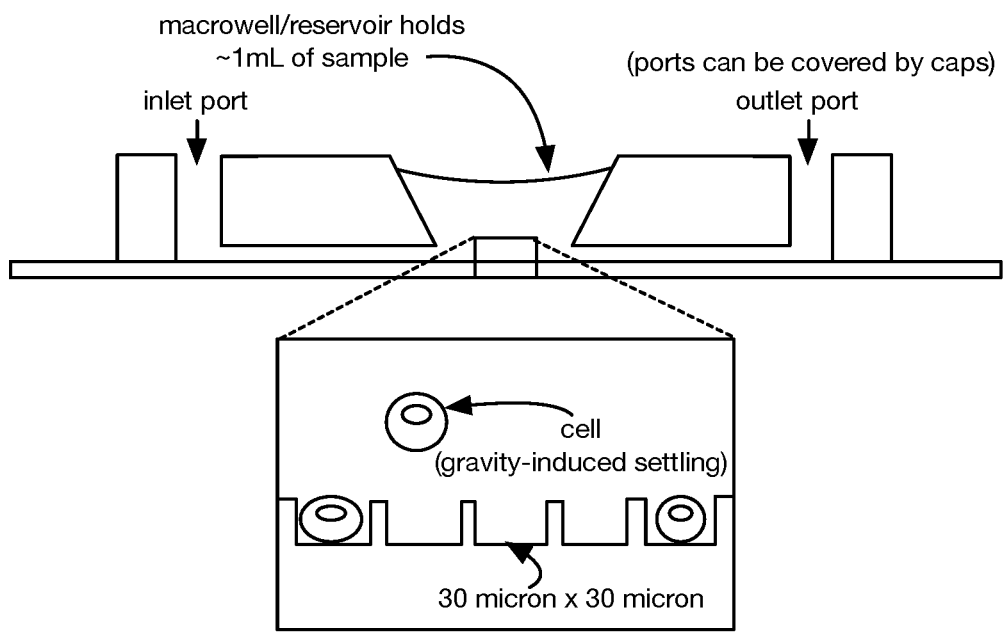

Furthermore, in a variation of the example described above, the array of 250,000 nanowells can be embossed into a plastic (e.g., material COP480R) using a photolithographic etching process. A reservoir can then be provided (e.g., glued) around the nanowell area region that allows a relatively large liquid sample to be placed during use. The specific example can further include two microchannels that serve as inlets and outlets to the macrowell comprising the nanowell region, as shown in FIG. 21A. Furthermore, as shown in FIG. 21B, a cell-containing sample, (e.g., up to 1 ml in volume), can be dispensed into the macrowell/reservoir formed by the recessed region of a plate of a fluid delivery model surrounding the nanowells. Cells present in the sample will settle down over time and reach the bottom of the microstructures. In specific applications, the settling time depends on the size of the cells, and typical cancer cells that are 10-25 microns in size will settle in about 30 minutes. Once the cells reach the bottom of the wells, they are captured in single cell format. Because the walls in between the nanowells are thin (e.g., 4-5 microns thick), most of the cells tend to settle inside the well as opposed to on top of the wells. In specific applications with cell-tracker stained cancer cells (SKBR3) spiked in 1 ml PBS, the system 100 demonstrated an over 90% capture efficiency.

In some variations, the set of wells 112 can further include a perimeter channel 150 surrounding the set of wells 112 and fluidly coupled to each well 113 in an exterior subset 115 of the set of wells 112 by way of at least one channel in the set of channels 140 of each well in the exterior subset 115 of the set of wells. Each substrate 105 of the system 100 can have a single set of wells 112, or can have multiple subsets of wells defined at the substrate in any suitable manner (e.g., in a radial configuration, in a rectangular configuration, in a linear configuration, in a curvilinear configuration, in a random configuration, etc.).

The set of wells 112 functions to receive the set of cells in at least one of single-cell format and single cluster format; however, the set of wells 112 can additionally or alternatively be configured to receive any other suitable type of particle, in any other suitable format. For instance, the set of wells 112 can be configured (e.g., sized, shaped) to receive mammalian cells, embyros, microspheres, particles, and cells conjugated to microspheres. Each well 113 in the set of wells 112 is preferably identical to every other well in the set of wells 112, and includes a base surface 120 defined within the substrate 105, and an open surface 130 directly opposing the base surface 120, defined at the broad surface 106 of the substrate 105. The base surface 120 is preferably parallel to the open surface 130; however, in some variations, the base surface 120 can alternatively be non-parallel to the open surface 130. Similar to the broad surface 106 of the substrate 105, the base surface 120 can be a planar surface or a non-planar surface, and in variations of the base surface 120 having a non-planar surface, the non-planar surface can include convex and/or concave portions having any suitable geometric characteristic. Additionally or alternatively, the base surface 120 can be any one or more of: textured (e.g., to facilitate desired fluid flow behavior, to attract or repel a given particle type, etc.), characterized by a desired porosity, characterized by a desired surface treatment, and characterized by any other suitable feature that facilitates cell reception and/or retention in any other suitable manner.

Figure 3A:
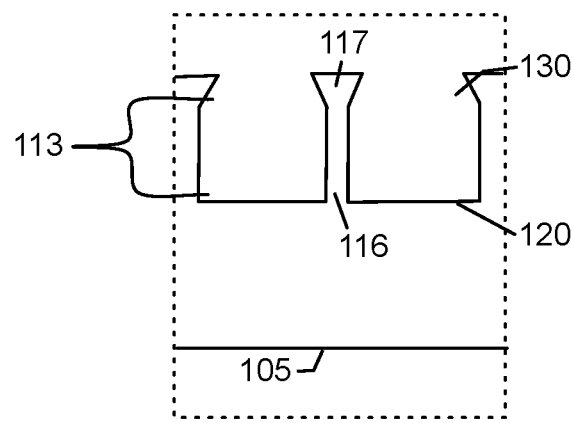
FIGS. 3A-3C depict variations of a portion of a system for isolating and analyzing cells.

The open surface 130 is preferably an opening in the substrate 105 that provides access to the base surface 120 of a well 113, and is configured to receive one of a single cell and a single cluster of cells from a direction perpendicular to the broad surface 106 of the substrate 105. As such, the open surface 130 can have a characteristic dimension (e.g., width, diameter, circumference, etc.) that is larger than, smaller than, or equal to that of the base surface 120. In an example for capture of circulating tumor cells (CTCs) from a sample in single-cell format, the characteristic dimension of either the base surface 120 or the open surface 130 can be 25 microns, and in variations of the example, the characteristic dimension(s) can have any dimension from 0.5 microns to 50 microns. In one example wherein the open surface 130 has a characteristic dimension smaller than that of the base surface 120, as shown in FIG. 3A, a well 113 can have a lip 117 that forms a boundary of the open surface 130 in order to provide a characteristic dimension that is smaller than that of the base surface 120. The lip 117 can be planar or non-planar, and can further facilitate retention of a single cell or a single cluster of cells at the well 113. The open surface 130 can, however, include any other suitable feature that facilitates cell reception and/or particle retrieval from the well 113 of the set of wells 112. The open area of the set of wells 112 (i.e., the sum total area of the open surface of each well in the set of wells) is preferably greater than 50% of the total area of the region of the substrate at which the wells are defined; more preferably, the open area is greater than 80% of the total area. However the open area can be any suitable fractional area or percentage of the total area of the substrate.

Figure 3B:
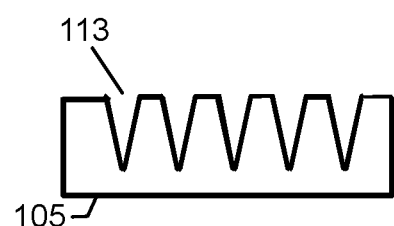
Figure 3C:
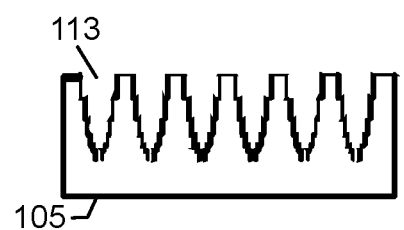

In relation to the base surface 120 and the open surface 130, each well 113 preferably has at least one wall 116 extending between the base surface 120 and the open surface 130, as shown in FIG. 3A, wherein the wall 116 at least partially separates the well 113 from at least one other adjacent well, defines a depth of the well, and is perpendicular to a plane defined by the open surface 130. The wall 116 can extend vertically from a plane defined by the open surface 130 to the base surface 120; as such, in some variations, a well 113 of the array 100 can be prismatic (e.g., cylindrical prismatic, hexagonal prismatic, polygonal prismatic, non-polygonal prismatic, etc.). However, the wall 116 can extend between the open surface 130 and the base surface 120 in any other suitable manner in other variations. For instance, the wall 116 can gradually reduce a characteristic dimension (e.g., diameter) of the well from the open surface to the base surface (e.g., by forming discrete steps, by gradually adjusting the characteristic dimension in a linear or a non-linear manner with any suitable slope, etc.), examples of which are shown in FIGS. 3B and 3C. However, in some variations, a well 113 may not have a well-defined wall 116 perpendicular to a plane defined by the open surface 130 (e.g., the base surface may extend in some manner directly to the open surface without forming a wall perpendicular to the open surface). In examples, the base surface 120 and the open surface 130 can be separated, with or without a wall, by a distance of between 0.5 microns to 50 microns (e.g., 25 microns for an application involving capture of CTCs).

While every well 113 in the set of wells 112 can be substantially identical, the set of wells 112 can alternatively include wells that are non-identical to each other by any suitable feature (e.g., morphological feature, mechanical feature, surface coating feature, thermal conductivity feature, electrical conductivity feature, etc.). As such, some variations of the system 100 can be configured to capture at least one of multiple particle types and particles in multiple types of formats, in addressable locations, for processing and analysis. In a first example, the set of wells 112 can include a first subset of wells 118 with wells having a first characteristic dimension (e.g., well diameter, well depth, well volume, etc.) in order to capture a first cell type in single cell format, and a second subset 119 with wells having a second characteristic dimension (e.g., well diameter) in order to capture a second cell type in single cell format. In the first example, the first subset 118 can be centrally located within the set of wells 112, and the second subset 119 can be peripherally located within the set of wells 112 and have a second characteristic dimension that is smaller than the first characteristic dimension, in order to facilitate capture of larger particles at a central portion of the set of wells 112 and smaller particles at a peripheral portion of the array 100 (e.g., in a cytospin application). In one variation of the first example, the set of wells 112 can include wells having a gradient of characteristic dimensions in a radial direction (e.g., larger well dimensions toward the center of the array and smaller well dimensions toward the periphery of the array). In other variations of the first example, the set of wells 112 can include wells having a gradient of any other suitable feature characteristic (e.g., morphological feature, mechanical feature, surface coating feature, thermal conductivity feature, electrical conductivity feature, etc.) in a radial direction. In other examples, the set of wells 112 can include wells having a distribution (e.g., gradient) of any suitable feature characteristic (e.g., morphological feature, mechanical feature, surface coating feature, thermal conductivity feature, electrical conductivity feature, etc.) along any suitable direction (e.g., linear direction, radial direction, circumferential direction, etc.).

Figure 4A:
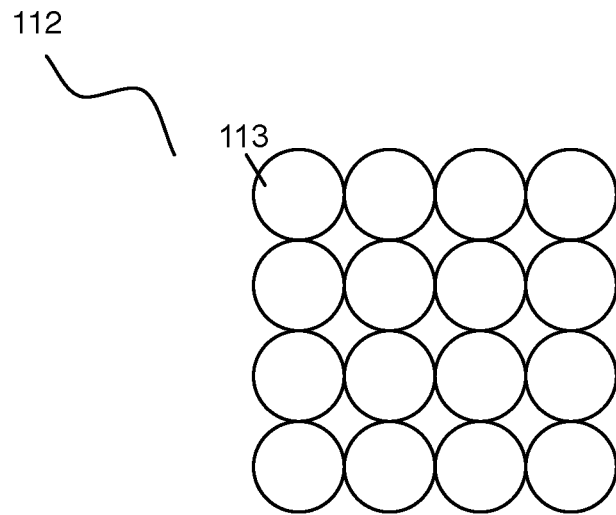
FIGS. 4A-4B depict example configurations of a portion of a system for isolating and analyzing cells.
Figure 4B:
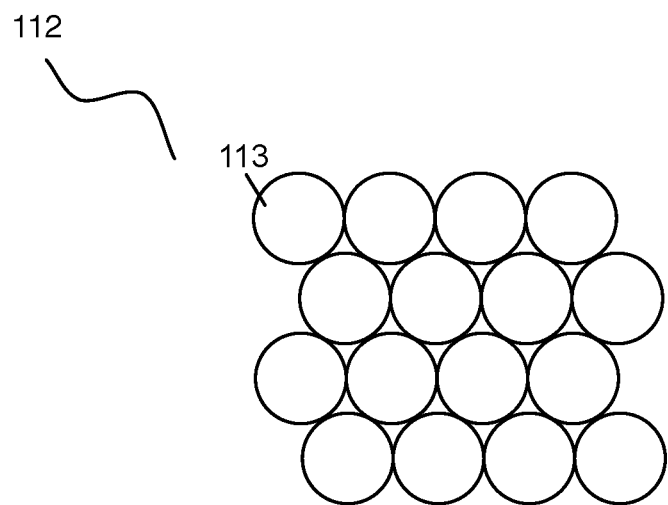
Figure 14:
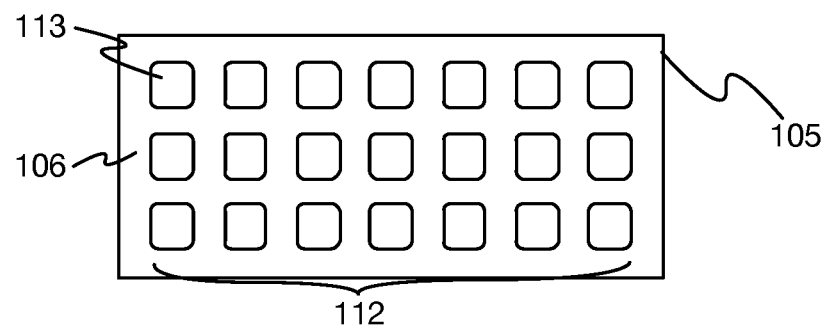
FIG. 14 depicts an example configuration of a portion of a system for isolating and analyzing cells.

Furthermore, the set of wells 112 is preferably arranged in a packed array, but can alternatively be arranged in any other suitable manner. In one example, the set of wells 112 can be arranged in a packed rectangular array, as shown in FIGS. 4A and 14. In another example, the set of wells 112 can be arranged in a closest packed array (e.g., hexagonal closest packed array), as shown in FIG. 4B. In another example, the set of wells 112 can be arranged in any suitable irregular or non-uniform manner, for instance, to facilitate fluid flow from one portion of the set of wells 112 to another portion of the set of wells 112. However, the set of wells 112 can alternatively be arranged with any suitable spacing between wells (e.g., in a packed or a non-packed configuration), and in any other suitable manner.

Figure 5:
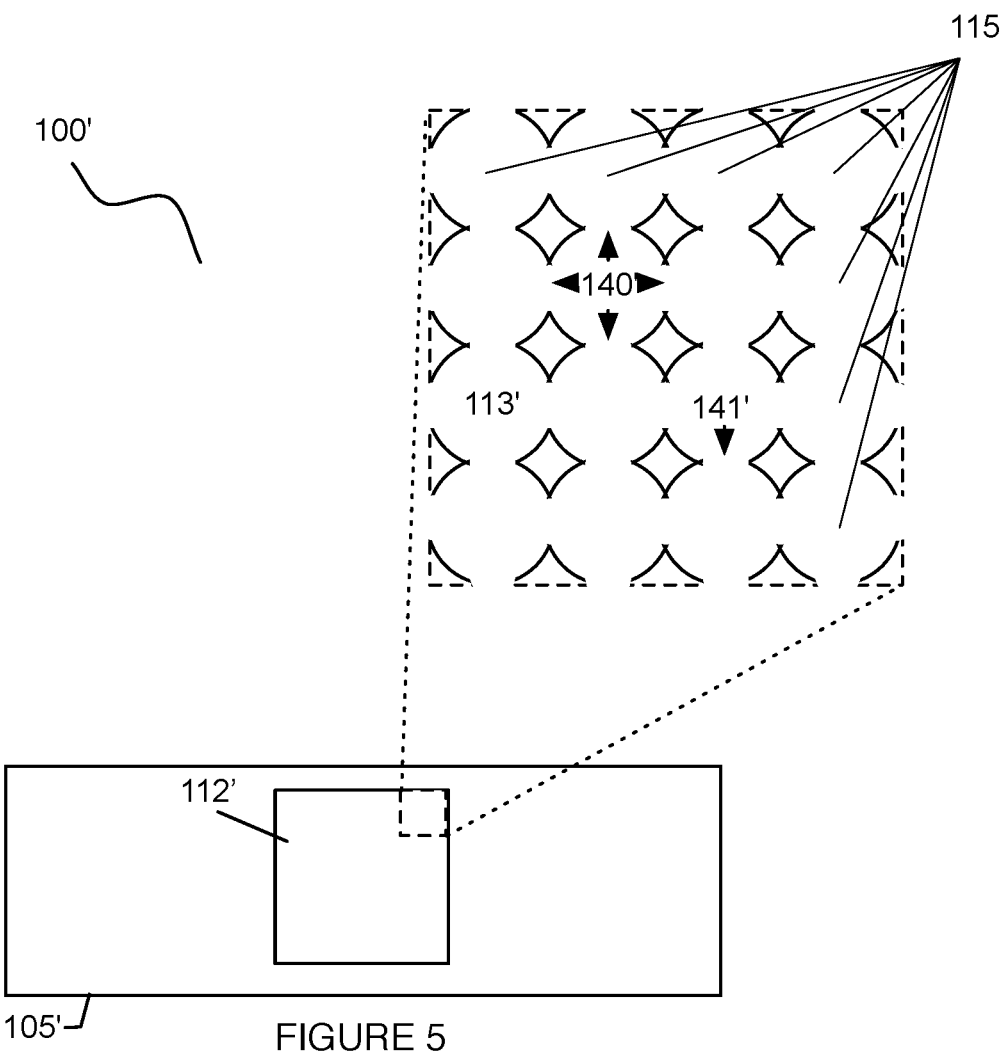
FIG. 5 depicts a specific example of a system for isolating and analyzing cells.

The set of channels 140 function to enable fluid flow exchange between at least two wells of the set of wells 112, and/or between one well of the set of wells 112 and another element of the system 100, while preventing migration of particle contents of a well 113 (e.g., a captured cell, a captured cell cluster). As such, a characteristic dimension (e.g., width, diameter) of each channel 141 in the set of channels 140 for a well 113 is preferably smaller than a characteristic dimension (e.g., width, depth) of the well 113 in order to enable retention of desired contents of a well 113. In some alternative variations, however, a well may be coupled to one or more channels having a characteristic dimension equal to or greater than that of a captured cell/cell cluster, in order to facilitate migration of a cell/cell cluster from one well to another well along a preferred direction. A channel 141 of a set of channels can extend from the open surface 130 of a well 113 to a base surface 120 of the well 113, such that a depth of the channel 141 is equal to the depth of the well 113. However, the channel(s) can alternatively have any other suitable depth (e.g., a depth less than that of the well) and be defined in relation to the open surface 130 and the base surface 120 of a well 113 in any other suitable manner. Preferably, every channel 141 in a set of channels 140 is identical, for a given well 113, in morphology (e.g., length, cross section); however, a set of channels 140 for a well 113 can alternatively include one or more non-identical channels 141 (e.g., a channel having a different length, a channel having a different cross section than other channels in a set of channels). The set of channels 140 can be arranged about a well 113 in a uniform radial pattern, can be arranged about a well 113 in a non-uniform radial pattern, or can be arranged about a well 113 in any other suitable manner to couple the well 133 to its adjacent well(s). However, in some variations, the set of channels 140 can be configured to couple each well to two adjacent wells (aside from an initial well and a terminal well, which would each only include a single channel), such that the set of wells 112 is coupled in series. In some variations, the channel(s) of a set of channels 140 can be defined within a region of the substrate 105 between adjacent wells, or can be defined by overlapping portions of adjacent wells, as shown in FIG. 5. In a specific example, a channel 141 can have a characteristic dimension of 5 microns, and in variations of the specific example, a channel 141, can have a characteristic dimension ranging from 0.5 microns to 50 microns. Alternatively, at least one well 113 in the set of wells 112 may not be coupled to every adjacent well in variations of the set of wells 112. Furthermore, some variations of the array may not include a set of channels 140 for any well 113 of the set of wells 112.

Figure 6:
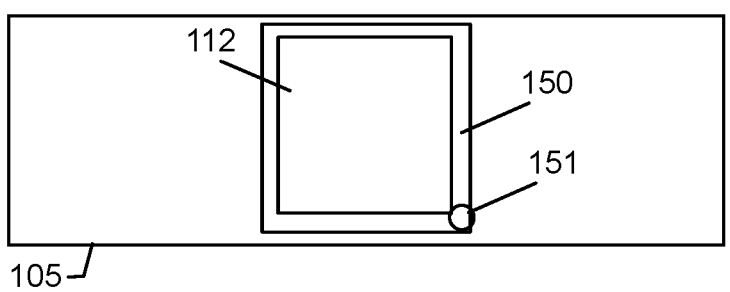
FIG. 6 depicts a variation of a system for isolating and analyzing cells.

As shown in FIGS. 1, 5, and 6, the system 100 can further include a perimeter channel 150 surrounding the set of wells 112 and fluidly coupled to each well 113 in an exterior subset 115 of the set of wells by way of at least one channel 141 in the set of channels 140 of each well in the exterior subset 115 of the set of wells 112. The perimeter channel 150 functions to enable modulation of an amount of fluid at the set of wells 112, such that an amount of fluid within the set of wells 112 can be reduced, maintained, or increased by way of the perimeter channel 150. As such, the perimeter channel 150 can receive and distribute process reagents throughout the set of wells 112, and/or facilitate removal of excess or used process reagents from the set of wells 112. The perimeter channel 150 can be at least partially enclosed by the substrate 105 or another element of the system 100, and coupled to a fluid port 151 that facilitates modulation of an amount of fluid at the array. As such, fluid can be delivered and/or removed from the set of wells 112 by way of the fluid port 151, in an automatic or manual manner (e.g., using a pump, using capillary soaking, etc.). Additionally or alternatively, the perimeter channel 150 can include open portions not enclosed by the substrate 105 that facilitate fluid level modulation with or without use of the fluid port(s), for instance, using capillary soaking or evaporation. In some variations, the perimeter channel 150 can be coupled to any other suitable portion of the set of wells 112 (e.g., a non-exterior subset of the array), in order to facilitate modulation of an amount of fluid at the set of wells 112.

In some variations of the system 100, one or more wells of the set of wells 112 can further include any other suitable element that facilitates stimulation and/or detection of a parameter (e.g., a cellular response parameter) at the well(s) of the set of wells 112. In one example, one or more wells of the set of wells 112 of the set of wells 112 can include an electrode embedded in the substrate 105 at a surface of the well 113 in order to facilitate detection of bioelectrical signals from contents of the well 113, and/or to facilitate stimulation of the contents of the well 113. In variations of the example, the electrode can be embedded with an exposed portion at least one of the base surface 120 and a wall 116 of the well 113. In other examples, the well(s) can be coupled to channels that facilitate delivery of process reagents to a cell/cell cluster at a well 113, or facilitate extraction of contents of a well 113 (e.g., processed intracellular contents) from the well 113. The system 100 can, however, include any other suitable element that facilitates processing and/or analysis of cells in at least one of single-cell format and single cluster format.

Figure 18:
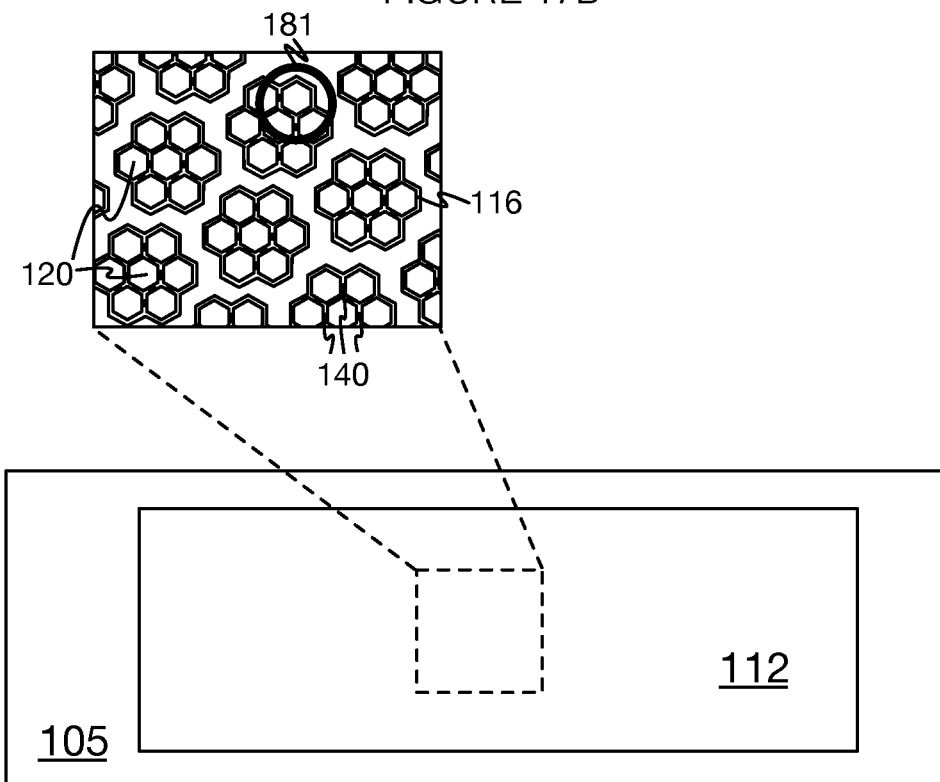
FIG. 18 depicts a zoomed in schematic representation of a specific configuration of a portion of a system for isolating and analyzing cells.
Figure 19:
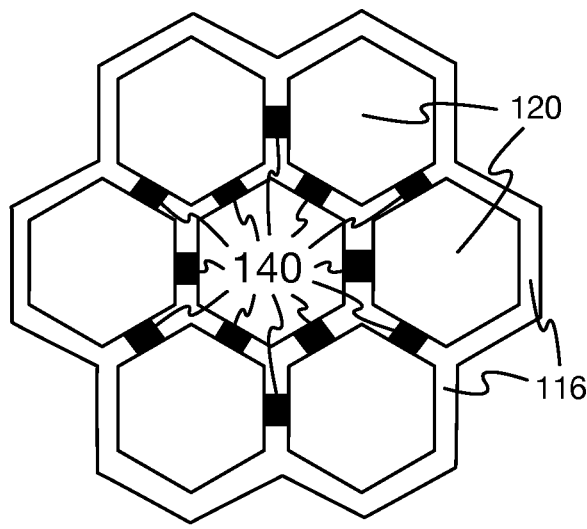
FIG. 19 depicts a schematic representation of a specific example configuration of a portion of a system for isolating and analyzing cells.

In a specific example configuration of the set of wells as shown in FIGS. 18 and 19, the wall of each well defines a hexagonal footprint about the base surface of the well. The set of wells is arrayed in a hexagonal close-packed configuration at the broad surface of the substrate, and the substrate defines 267,000 such hexagonal wells. The wells are organized into groups of seven wells each, including one central well and six peripheral wells. Each of the peripheral wells of the group includes three channels, connecting the peripheral wells to the two adjacent peripheral wells and the central well. The central well includes six channels. The channels of each well are defined by a number of openings (equal to the number of channels) in the wall of each well. The channels of the group of wells functions to fluidically interconnect the group of seven wells. Each group is fluidically isolated from the other groups (i.e., there are no channels connecting wells of different groups).

1.3 System—Fluid Delivery Module

Figure 7A:
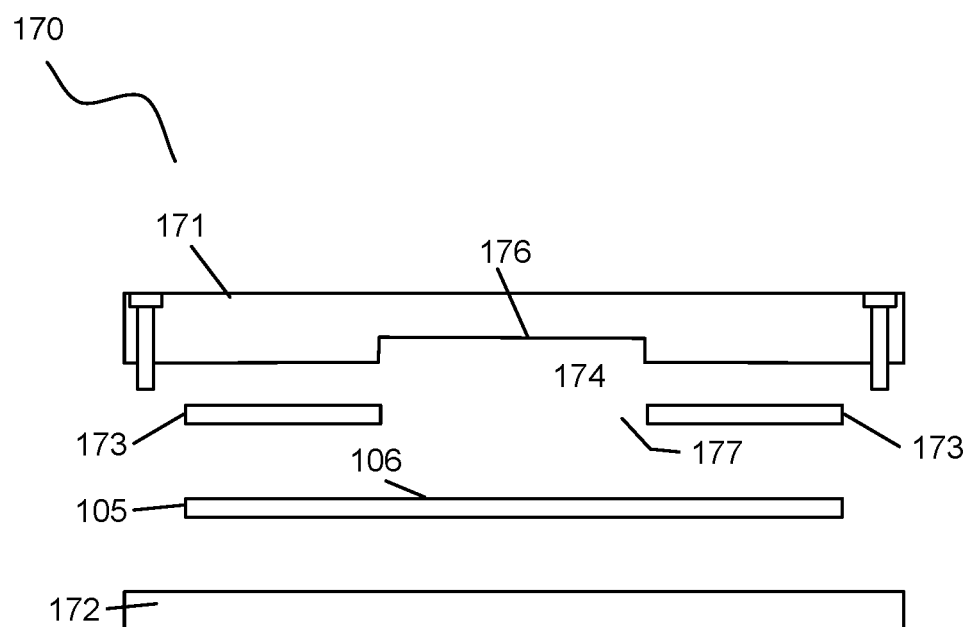
FIGS. 7A and 7B depict additional portions of an embodiment of a system for isolating and analyzing cells.
Figure 7B:
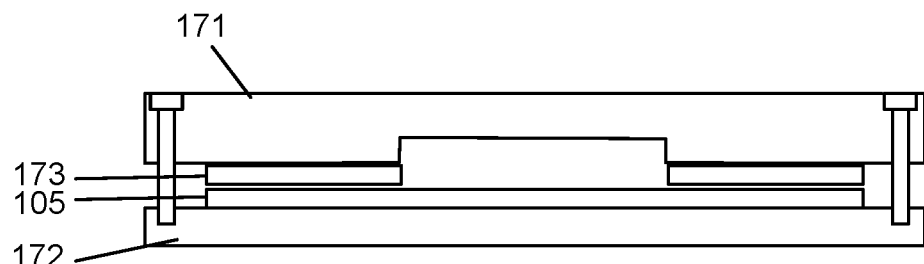

Also shown in FIGS. 1, 7A, and 7B, the system 100 can include a fluid delivery module 170 configured to couple to the substrate 105. The fluid delivery module 170 functions to transfer a sample containing the set of cells and/or another fluid to the set of wells 112. As such, the fluid delivery module can define an inlet 111, an outlet 114, and fluidic guides and/or structures that enable sample transfer into, out of, and throughout various portions of the system. As shown in FIGS. 7A and 7B, the fluid delivery module 170 can include a first plate 171 configured proximal the broad surface of the substrate 105, a second plate 172 configured proximal a surface of the substrate 105, directly opposing the broad surface of the substrate 105, and a clamping module configured to couple the first plate 171 to the second plate 172, thereby positioning and/or aligning the substrate 105 between the first plate 171 and the second plate 172. Alternatively, however, the first plate 171 can be directly coupled to the substrate 105 and/or to any other suitable element of the system 100, such that the fluid delivery module 170 omits a second plate 172. As such, the fluid delivery module 170 faciliates positioning of the substrate 105 to receive and/or seal the sample or fluid at the set of wells 112 (e.g., with a compressive force, with a hermetic seal, etc.). Additionally or alternatively, the fluid delivery module 170 can include an absorbant layer 173 configured between the first plate 171 and the substrate 105, that facilitates modulation of an amount of fluid at the set of wells 112.

As shown in FIG. 7A, the first plate 171 can have a rectangular footprint that spans the broad surface 106 of the substrate 105. However, the first plate 171 can alternatively have any other suitable footprint (e.g., non-rectangular footprint, circular footprint, ellipsoidal footprint, etc.) configured to span all or a portion of the broad surface 106 of the substrate 105. The first plate 171 preferably has a recess 174 facing the broad surface 106 of the substrate 105, such that the recess 174 and the broad surface 106 cooperatively define a lumen that can be fluidly connected to an inlet and outlet of the fluid delivery module. The recess 174 preferably functions as a reservoir to temporarily hold a sample and/or a processing reagent proximal to the set of wells 112 (e.g., in a fluid layer occupying the lumen defined by the recess and the broad surface of the substrate). As such, the recess 174 preferably spans the set of wells 112, and aligns with the array when the first plate 171 is coupled to the substrate 105. The lumen can have any suitable volume, preferably defined by the product of the gap distance between the base surface of the recess and the projected area of the recess. The gap distance is preferably between 25 microns and 10 mm, but can alternatively be any suitable distance.

In one variation, the recess 174 can be a rectangular recess defined within the surface of the first plate 171 facing the substrate 105. Furthermore, the recess can have a substantially planar base surface 176, as shown in FIG. 7A, or any other suitable base surface 176 (e.g., non-planar base surface). However, the recess 174 can alternatively have any other suitable morphology. Additionally or alternatively, the recess 174 can include a sealing element (e.g., o-ring, sealant, etc.) surrounding a region of the recess 174 proximal the substrate 105, in order to provide a hermetic seal upon coupling of the first plate 171 to the substrate 105. However, the first plate 171 can alternatively be configured in any other suitable manner.

The second plate 172 is configured proximal to a surface of the substrate 105, directly opposing the broad surface of the substrate 105, and functions to provide a base to which the first plate 171 can be coupled, thereby positioning the substrate 105 between the first plate 171 and the second plate 172. The second plate 172 preferably provides a complementary surface to which the surface of the substrate 105, opposing the broad surface 106, can be coupled. In one variation, the second plate 172 is a substantially planar, in order to provide a surface to which a planar surface of the substrate 105 (e.g., a planar surface directly opposing the broad surface of the substrate) can be coupled; however, the second plate 172 can be configured relative to the substrate 105 in any other suitable manner. Furthermore, the second plate 172 can include an aligning element that facilitates alignment of the second plate 172 relative to the substrate 105 and/or to the first plate 172. In variations, the aligning element can include any one or more of: a protrusion and/or a recess at the second plate 172 that facilitates alignment, a track that facilitates alignment, a magnetic element, and any other suitable alignment element.

In one variation, the first plate 171 is preferably coupled to the second plate with a coupling mechanism that can include one or more of: a pin, a screw, a magnetic coupler, a clamp, and any other suitable coupling mechanism. To prevent obstruction, the coupling mechanism can be located at peripheral portions of the system (e.g., at peripheral portions of the first plate 171, the second plate 172, and/or the substrate 105), or at any other suitable location that does not interfere with function of the substrate. Alternatively, some variations of the system 100 may omit the second plate 172, and have direct coupling between the first plate 171 and the substrate 105 in any suitable manner.

Some variations of the fluid delivery module 170 can include an absorbant layer 173 situated between the first plate 171 and the substrate 105. The absorbant layer 173 functions to facilitate modulation of an amount of fluid at the set of wells 112, during a process that distributes the cells/cell clusters in single cell and/or cluster format at the array. As such, the absorbant layer 173 can be composed of any suitable absorbant material configured to absorb liquids, without receiving or retaining target cells of the sample. In some variations, the absorbant material can include any one or more of: a hydrogel having a network with pore sizes smaller than a characteristic dimension of a target cell, a porous material (e.g., a sponge), a hydrophilic material, and any other suitable absorbant material. Additionally or alternatively, in some variations, the absorbant layer 173 can be configured to attract, receive, and/or retain undesired particles from a sample, such that that the absorbant material facilitates filtration or segregation of undesired particles from the target particles of a sample. In such variations, the absorbant layer 173 can be configured to receive or retain undesired particles according to affinity molecule-based capture, pore size-based capture, adhesion behavior, and/or any other suitable mechanism.

As shown in FIG. 7A, the absorbant layer 173 is preferably a planar layer 173 in contact with both the first plate 171 and the substrate 105 upon coupling of the first plate 171 to align the recess 174 with the set of wells 112. However, the absorbant layer 173 can alternatively have any other suitable morphology. Additionally, the absorbant layer 173 preferably has an opening 177 aligned with the recess 174 of the first plate 171, such that fluid within the reservoir formed by the recess 174 can reach the set of wells 112 through the opening 177 of the absorbant layer 173. The opening can be a single opening, or can comprise any suitable number of openings that provide access between contents of the recess 174 and the set of wells 112 of the substrate 105. However, the abosrbant layer 173 can alternatively be configured in any other suitable manner.

Figure 17A:
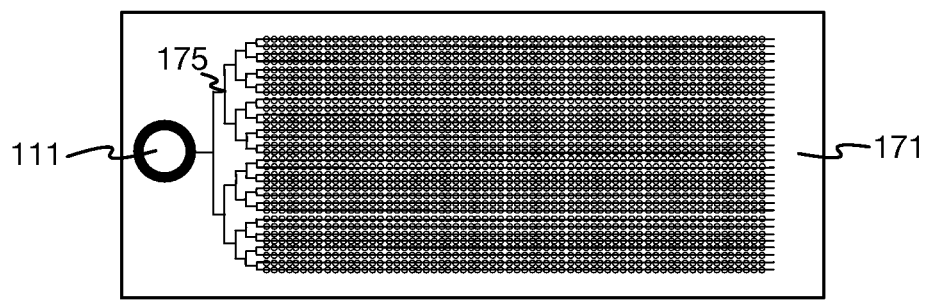
FIG. 17A-B depict a top and bottom view, respectively, of an example configuration of a portion of a system for isolating and analyzing cells.
Figure 17B:
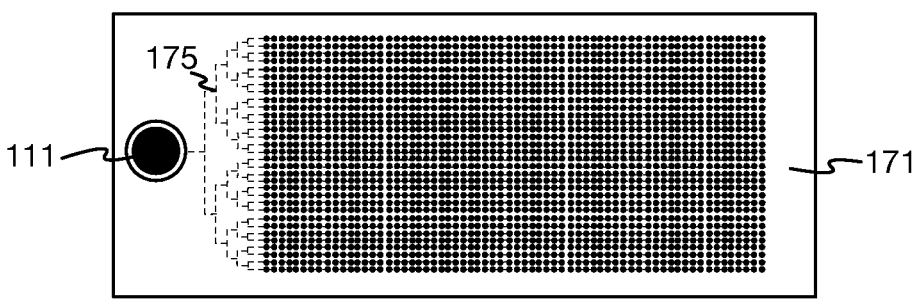

As shown in FIGS. 17A and 17B, some variations of the fluid delivery module 170 can include a set of fluid pathways 175 linking an inlet in of the system 100 to each of the set of wells 112. The set of fluid pathways functions to route desired fluids (e.g., reagent-containing fluids, sample containing fluids, etc.) to the wells 112. The set of fluid pathways can have any suitable correspondence with the set of wells; for example, there may be one fluid pathway per single well 113, multiple fluid pathways per single well 113, and/or one fluid pathway connected to multiple wells. In another example, the set of fluid pathways is a network of fluid pathways that branches from a single fluid pathway, connected to the inlet, into a set of fluid pathways connected to each well individually such that the total length of any fluid pathway between the inlet and a well is substantially equal in length (e.g., exactly equal length, equal to within 10-100 microns, equal to within a characteristic length for a given flow rate and pathway cross-section, equal to within any suitable threshold length, etc.). The set of fluid pathways can additionally or alternatively include fluid pathways that connect groups and/or subsets of wells to an inlet, as well as to other groups and/or subsets of wells. Each of the subsets thus connected can include an identical number of wells, but can alternatively have differing numbers of wells in each subset connected by the set of fluid pathways.

Figure 8:
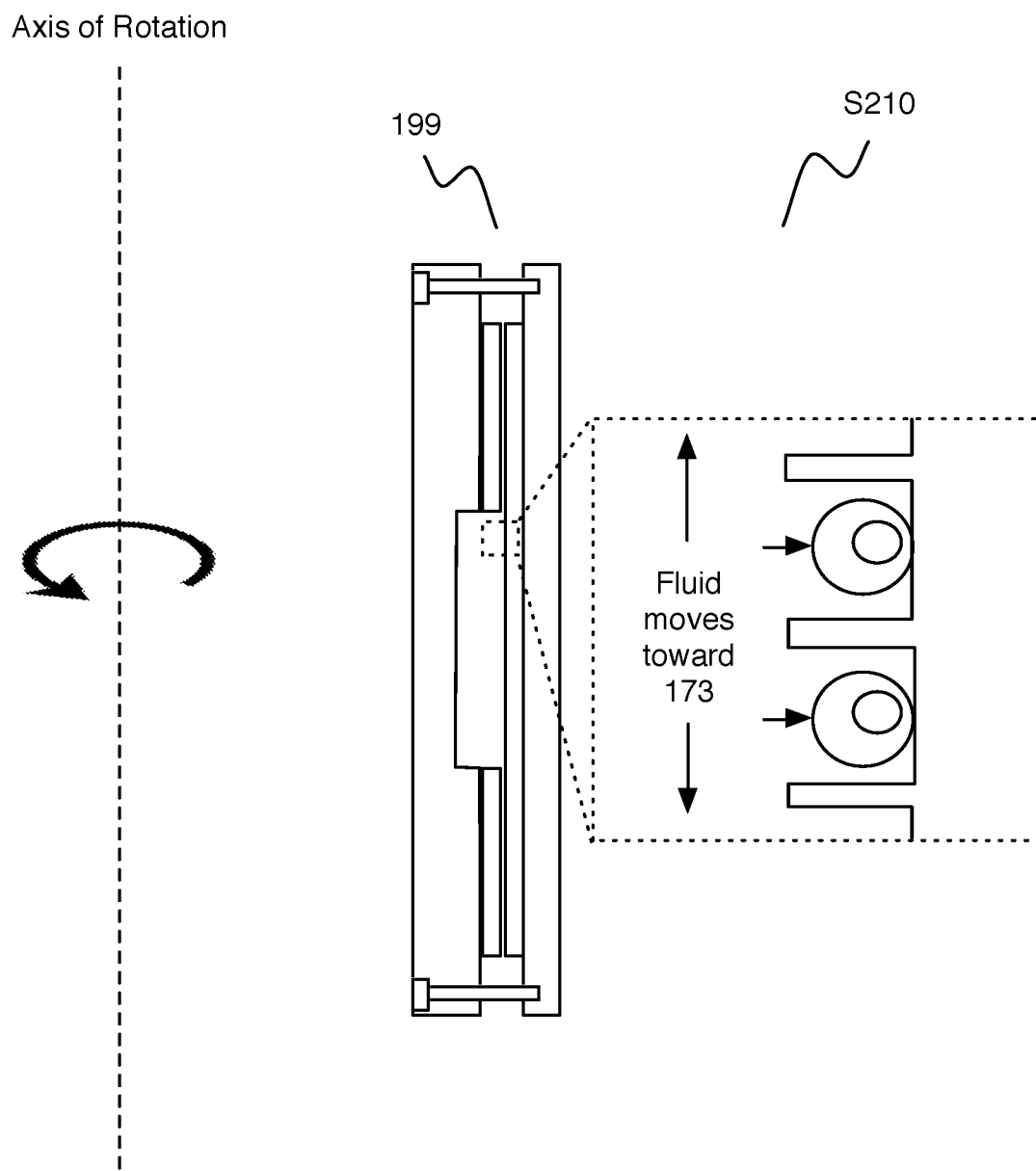
FIG. 8 depicts a variation of a process involving a system for isolating and analyzing cells.

In one example application, as shown in FIG. 8, an assembly 199 comprising the first plate 171, the absorbant layer 173, the substrate 105, and the second plate 172 can be coupled together and rotated about an axis of rotation parallel to and offset from the broad surface of the substrate 105, such that the normal defined by the broad surface 106 of the substrate 105 passes through the axis of rotation. As such, during rotation of the assembly 199, fluid within a reservoir formed by the recess 174 of the first plate 171 can be pushed toward the wells of the set of wells 112 by centripetal force (e.g., to capture cells at the wells), while excess fluid can flow into the absorbant layer 173. However, in variations of the example application, the assembly 199 can be rotated about any other suitable axis, and/or capturing of cells at the set of wells 112 can be performed in any other suitable manner.

In another example, the fluid delivery module comprises the first plate 171, and the first plate 171 defines an inlet and an oulet. The plate further defines a recessed region that is fluidly connected to the inlet, and that faces the broad surface of the substrate so as to define a contiguous lumen cooperatively with the set of wells 112. The fluid delivery module is operable in a cell capture mode, in which a fluid sample containing a collection of single mammalian cells is flowed into the lumen between the inlet and the outlet (e.g., by a pressure differential). In this example, the fluid sample is flowed substantially parallel to the broad surface of the substrate. The sample is flowed at a flowrate (e.g., 1 milliliter per second, 1 millileter per minute, etc.), and the flowrate is selected (e.g., controlled) such that the combination of vertical forces on the single cells (e.g., gravitational, buoyancy, etc.) is directed toward the broad surface, and is greater the lateral pressure forces from the surrounding fluid so as to promote settling of the single cells into the set of wells from the laterally flowing sample.

Figure 15:
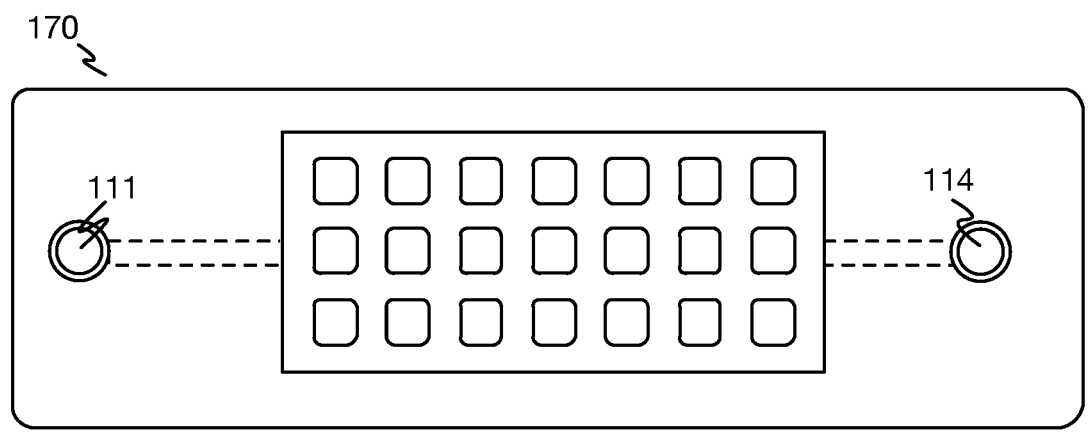
FIG. 15 depicts an example configuration of a portion of a portion of a system for isolating and analyzing cells.
Figure 16:
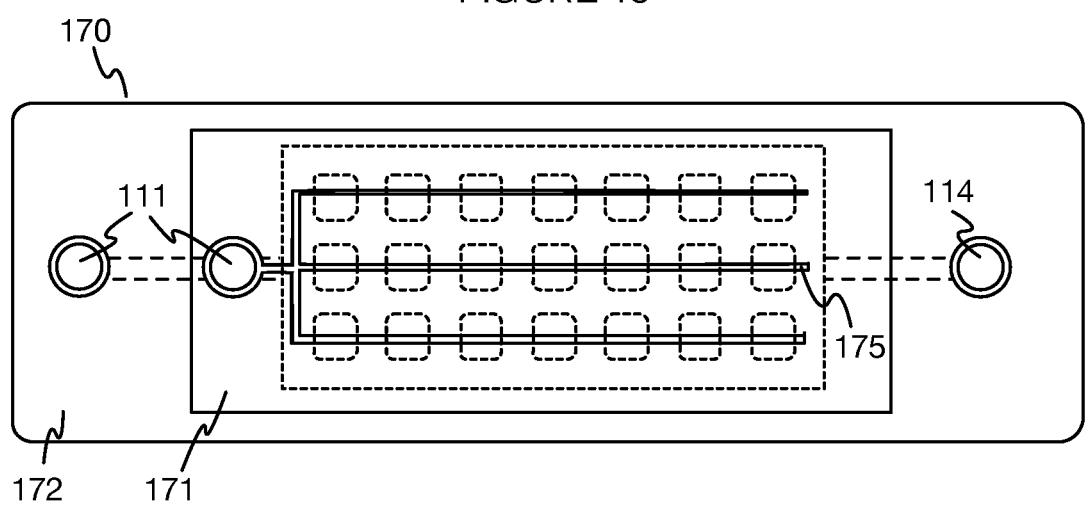
FIG. 16 depicts an example configuration of a system for isolating and analyzing cells.

In another example, as shown in FIGS. 15 and 16, the fluid delivery module comprises a first and second plate configured about the substrate at opposing sides. The first plate defines an inlet and a set of fluid pathways, configured to deliver fluids from the inlet to each of the set of wells of the substrate. The second plate defines an inlet and an outlet, as well as another set of fluid pathways configured to deliver fluid to the set of wells 112 as well as between the inlet and the outlet. An example mode of operation of this example configuration includes flowing a fluid reagent into the inlet of the first plate, and applying a pressure gradient between the inlet and outlet of the second plate to expel the fluid from the fluid delivery module after delivery to the set of wells 112.

1.4 System—Cell Removal Module

Figure 9:
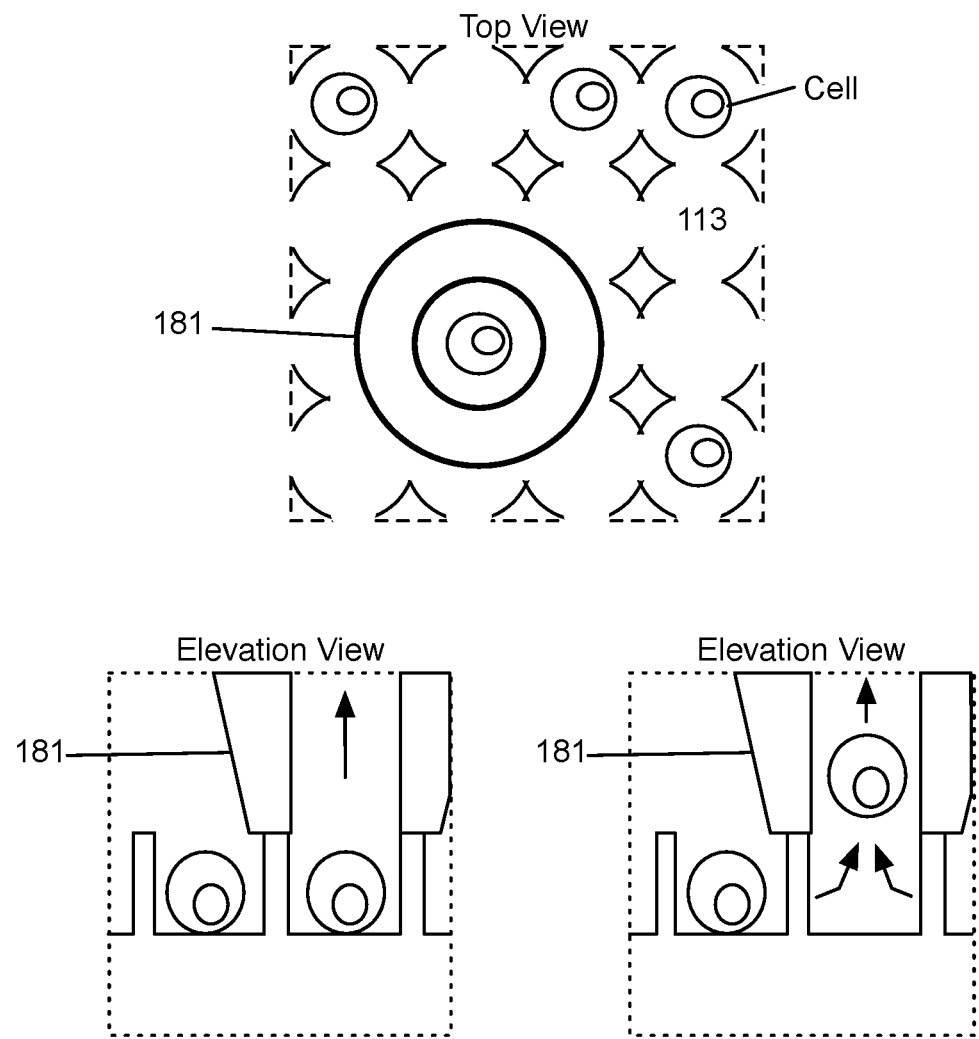
FIG. 9 depicts an additional portion of an embodiment of a system for isolating and analyzing cells.

Also shown in FIGS. 1 and 9, the system 100 can further include a cell removal module 180 (e.g., cell retrieval subsystem) that functions to extract at least one of a single cell and a cell cluster from a well 113 of the array. While an individual cell from a single well 113 is preferably selectively removed, the cell removal module 180 can facilitate simultaneous multiple cell/cell cluster removal from the set of wells 112. The cell/cell cluster is preferably removed by applying a removal force to the cell. The removal force is preferably applied by aspirating the contents out of a well 113 (i.e., using a negative pressure); however, the removal force can additionally or alternatively be applied by pumping fluid through the set of wells 112 (e.g., by way of a perimeter channel 150) to provide a positive pressure that drives the cell/cell cluster from the well 113. In one variation, the pump pressure provided by a pump mechanism at the cell removal module 180 is less than 10,000 Pa, and in a specific variation, the provided pump pressure is 6,000 Pa. However, any other suitable pump or aspiration pressure can be used.

In some variations, the cell removal module 180 can comprise a cell extractor 181. The cell extractor 181 functions to selectively remove one or more isolated cells from an addressable location within the system 100. The cell extractor 181 is preferably configured to remove a cell/cell cluster from a single well 113, but can alternatively be configured to simultaneously remove multiple cells/cell clusters from multiple wells 113. The cell removal module 180 is preferably operable in an extraction mode, wherein in the extraction mode the cell removal module 180 extracts at least one of a set of single cells from a well of the set of wells, along a direction normal to the base surface of the well. In the extraction mode, the fluid delivery module is preferably removed from the substrate; however, the fluid delivery module can alternatively remain coupled to the substrate when the cell removal module is operated in the extraction mode.

In a first variation of the cell extractor 181, the cell extractor 181 is configured to access the set of wells 112 from a direction normal to the broad surface 106 of the substrate 105. The cell extractor 181 preferably removes the cell/cell cluster in a substantially normal direction from the broad surface 106 of the substrate 105, but can alternatively remove the cell/cell cluster in an angled direction relative to the broad surface 106 of the substrate 105. The cell extractor 181 preferably includes a hollow channel (e.g., of a micropipette, capillary tube, etc.) that accesses the set of wells 112 and defines a substantially fluidly isolated volume in fluid communication with one or more wells. The hollow channel can include one or more sealing elements at the tip 182 (e.g., a polymeric coating or adequate geometry) that facilitate fluid seal formation with the well(s) 113. The cell extractor 181 preferably tapers from a proximal end to the tip 181, in order to provide an adequate geometry to receive contents of a well 113 into the cell extractor 181; however, the cell extractor 181 can alternatively have any other suitable form. As such, the hollow needle is preferably configured to form a substantially fluidly isolated volume within a well 113 of interest, and a low-pressure generator (e.g., a pump) is then used to aspirate the retained cell/cell cluster out of the well 113, through the hollow channel, and into a cell collection volume of the cell extractor 181. In one variation, the cell extractor 181 is a micropipette having a height of 200 micrometers and a hollow channel diameter of 25 micrometers; in another variation, the cell extractor 181 is a capillary tube having a channel diameter of 150 micrometers. In another variation, the wells of the set of wells 112 are grouped such that each group may be circumscribed by a closed curve in the plane parallel to the broad surface of the substrate, and the cell extractor 181 has an inner diameter that is smaller than the largest chord of the closed curve. However, other variations of these specific examples can have any other suitable defining dimensions.

The cell extractor 181 can be manufactured using microfabrication techniques, or can additionally or alternatively be injection molded, laser cut, stamped, or manufactured using any other suitable manufacturing technique. In one variation of hollow needle manufacture, a lumen is preferably etched into a substrate, such as silicon, using etching techniques such as deep reactive ion etching (DRIE), plasma etching, or any other suitable etching method. This step is preferably utilized with a mask that covers the portions of the substrate 105 to be protected. The walls and associated profiles are then preferably manufactured through isotropic etching of the substrate 105 utilizing a corrosive liquid or plasma, but any other suitable isotropic material removal method can be used. A mask is preferably used to protect the puncture end. Multiple hollow needles are preferably simultaneously manufactured as an array 200, but can alternatively be individually manufactured. The cell extractor 181 can, however, comprise any other suitable cell removal tool such as that described in U.S. application Ser. No. 13/557,510, entitled "Cell Capture System and Method of Use" and filed on 25 Jul. 2012, which is herein incorporated in its entirety by this reference.

Cell removal from the system 100 is preferably automated, but can additionally or alternatively be semi-automated or manual. Furthermore, cell removal can be performed along with cell identification, comprising automatic fixing, permeabilzation, staining, imaging, and identification of the cells removed from the set of wells 112 through image analysis (e.g., through visual processing with a processor, by using a light detector, etc.) or in any other suitable manner. The cell removal module 180 can be configured to facilitate advancement of a cell extractor 181 to a well 113 containing a cell/cell cluster of interest, for instance, with an actuation subsystem. The cell removal module 180 can additionally or alternatively be configured to facilitate cell removal method selection and/or cell removal tool selection. In another variation, cell identification at the cell removal module 180 can be semi-automated, and cell retrieval can be automated. For example, cell staining and imaging can be done automatically, wherein identification and selection of the cells of interest can be done manually. In another variation, all steps can be performed manually. However, any combination of automated or manual steps can be used.

1.5 System—Encapsulation Module

Additionally or alternatively, the system 100 can include an encapsulation module 190 configured to encapsulate the set of cells at the set of wells 112, and facilitate delivery of reagents to encapsulated cells of the set of cells at the set of wells 112. In one variation, the encapsulation module 190 can include a first encapsulation layer 191 coupled to the substrate 105 proximal the broad surface 106 of the substrate 105, that functions to seal cells captured at the set of wells 112 within an encapsulation matrix 199. As such, the first encapsulation layer 191 can form a boundary opposing the base surfaces 120 of each well 113 in the set of wells 112. The first encapsulation layer 191 is preferably an optically clear laminate, in order to facilitate visualization of contents of the set of wells 112; however, the first encapsulation layer 191 can alternatively comprise any other suitable material. Furthermore, the first encapsulation layer 191 can be reversibly removed and/or applied to the set of wells 112, in order to facilitate access to encapsulated contents of the set of wells 112.

Figure 10:
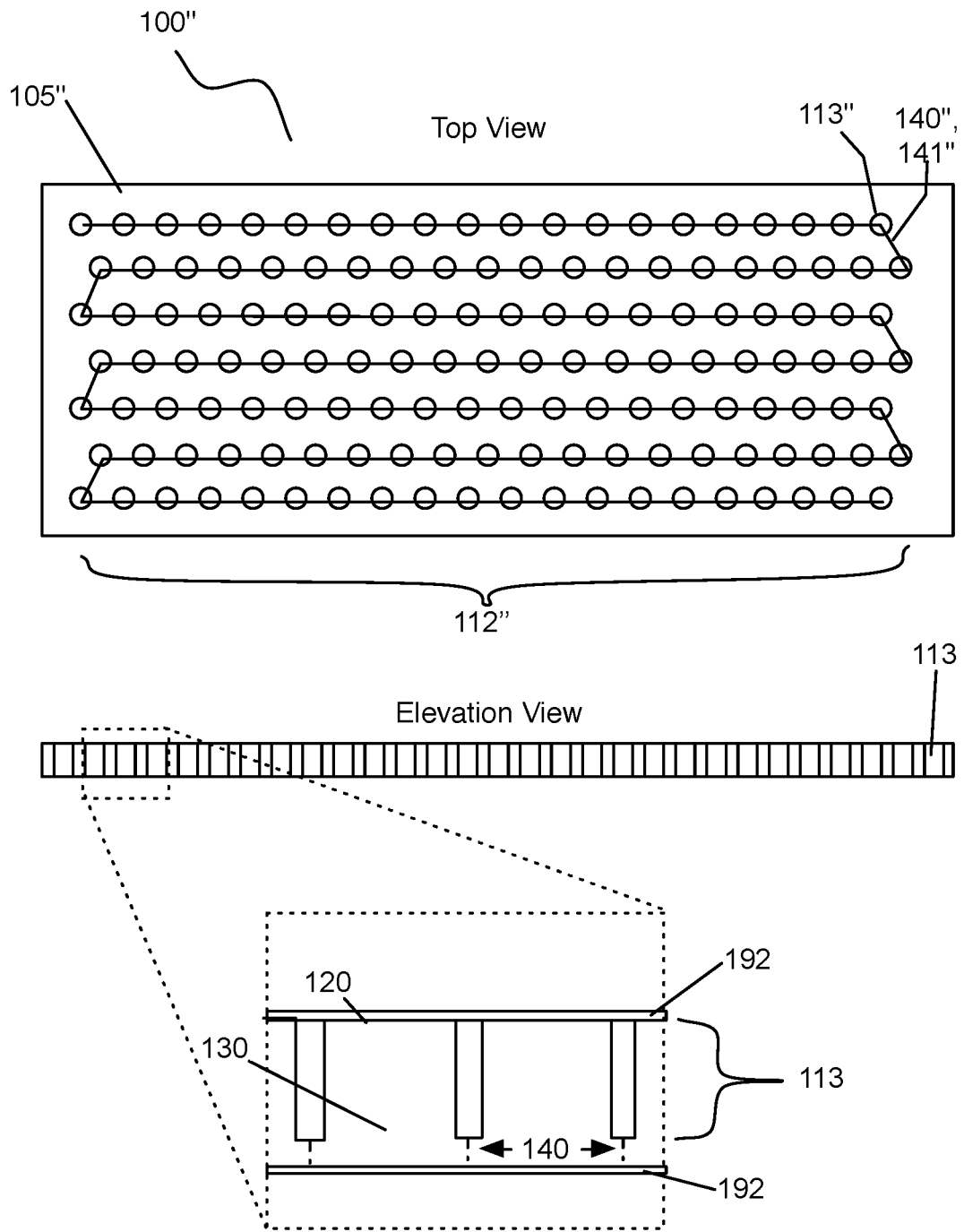
FIG. 10 depicts a specific example of a system for isolating and analyzing cells.
Figure 11:
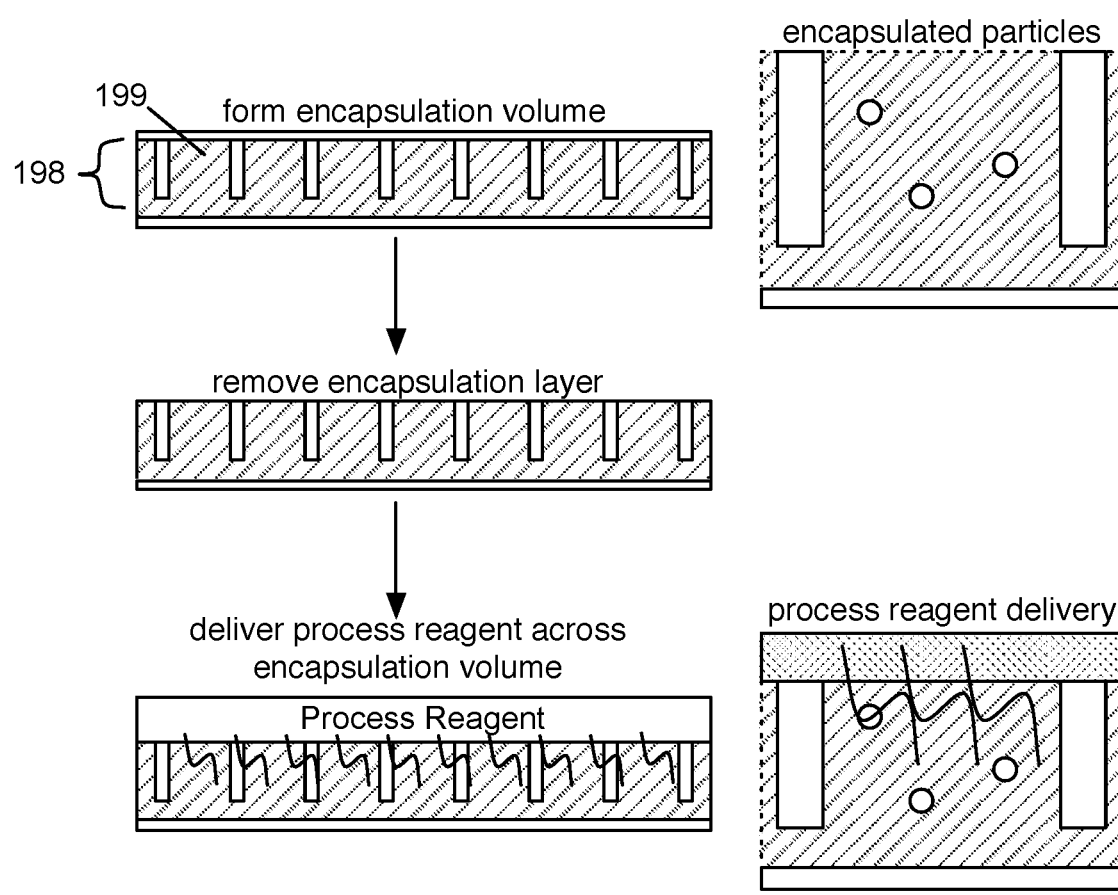
FIG. 11 depicts an additional portion of an embodiment of a system for isolating and analyzing cells.

In one variation, as shown in FIGS. 10 and 11, an encapsulation matrix 199 can be flowed into the set of wells 112 with the encapsulation module 190 at any suitable portion of the set of wells 112, forming an encapsulation volume 198 spanning the set of wells 112 and the set of channels 140 for each well 113 in the set of wells 112, up to the first encapsulation layer 191. The encapsulation matrix 199 preferably isolates a well 113 within a set of wells 112. The encapsulation matrix 501 preferably has a flow state and a set state, wherein any one or more of: a photochemical reaction, phase transition, thermochemical reaction, polymerization reaction and any other suitable reaction switches the encapsulation matrix 199 from the flow state to the set state. In the flow state, the encapsulation matrix 199 is preferably substantially viscous, such that the encapsulation matrix 199 does not flow into the wells 113 during introduction into the system 100. In the set state, the encapsulation matrix 199 is preferably a solid or gel that prevents particle egress from the wells 113 (e.g., egress of cells and/or large nucleic acid molecules from the pores), and is preferably porous or selectively permeable to permit small molecule, buffer, and reagent penetration therethrough. In one variation, the encapsulation matrix 199 is a microporous agarose gel, and in another variation, the encapsulation matrix 199 is a photopolymerizable hydrogel, such as PEG or polyacrylamide with photoinitiator; however, the encapsulation matrix 199 can alternatively be any suitable material with any other suitable polymerization agent.

In some variations, the encapsulation module 190 can additionally include a second encapsulation layer 192 forming the base surfaces 120 of the set of wells 112 of an array, such that the base surfaces 120 are not directly defined within the substrate 105, but at the second encapsulation layer 192. As such, the second encapsulation layer 192 can form a second boundary defining the base surfaces 120 of each well 113 in the set of wells 112, thereby partially bounding the encapsulation volume 198. The second encapsulation layer 192 is preferably an optically clear laminate, in order to facilitate visualization of contents of the set of wells 112; however, the second encapsulation layer 192 can alternatively comprise any other suitable material. Furthermore, the second encapsulation layer 192 can be reversibly removed and/or applied to the set of wells 112, in order to facilitate access to encapsulated contents of the set of wells 112.

Preferably, as shown in FIGS. 10 and 11, the encapsulation module 190 is configured such that diffusion of one or more reagents through the encapsulation volume 198 occurs upon removal of the second encapsulation layer 192 (e.g., in a direction from the base surface of a well toward the open surface of the well) from the substrate 105; however, the encapsulation module can additionally or alternatively be configured such that diffusion of one or more reagents through the encapsulation volume 198 occurs upon removal of the first encapsulation layer 191 (e.g., in a direction from the open surface of the well toward the base surface of the well) from the substrate 105. As such, removal of one or both of the first encapsulation layer 191 and the second encapsulation layer 192 from the substrate 105 can provide access of one or more reagents, through the encapsulation matrix 199, to captured contents at the set of wells 112. In examples, such processing reagents can include any one or more of: stains (e.g., cell-specific stains), cocktails (e.g., antibody cocktails), lysing reagents, fixing reagents, permeabilization reagents, culture reagents (e.g., media), and any other suitable process reagent. The reagent(s) can be delivered through the encapsulation volume 198 by applying pressure (e.g., positive pressure, negative pressure) and/or by passive diffusion. However, the encapsulation module 190 can alternatively be configured in any other suitable manner.

1.6 System—Additional Elements

The system 100 can additionally include thermal control module that functions to heat and/or cool the substrate and its contents, in order to control the temperature of contents of the set of wells and/or fluid delivery module during operation of the system 100. The thermal control module preferably includes a heater, but can additionally or alternatively include any suitable temperature control mechanism (e.g., an electrothermal cooling plate). In variations, the heater can include a low-mass heater that interfaces with substrate 105 for thermocycling or incubation (e.g., of PCR components, reagents, and/or sample), and in a specific example, the heater can comprise an aluminum heater coupled to a resistive power resistor (7 ohms) and a 2-wire 100-ohm RTD, wherein the heater elements are connected to an in-house heater driver and temperature controller. A PWM signal of 12 volts is provided across the heating element to heat the aluminum heater. The RTD provides temperature sensing and a control algorithm is used to modulate the temperature. During cooling, heating is stopped and fan is turned on to remove heat. Because the thermal mass is small, heating between anneal temperature (~60 C) and denaturation (~94 C) can be achieved in 20 seconds and cooling from 94 C to 60 C can be achieved in 40 seconds with the specific example.

The heater is preferably a resistive electrothermal heating element, but can alternatively or additionally include an induction heating element, convective heating element, optical heating element, or any other suitable heating mechanism. The heater is preferably arranged adjacent to a bottom surface of the substrate, but can alternatively be positioned adjacent to a top surface of the substrate, distal the substrate (e.g., in variations wherein the heater includes non-contact heating mechanisms) at either the bottom or top surface of the substrate, or in any other suitable location. The heater can be used to perform various in situ assays at the substrate that may require elevated temperatures (e.g., polymerase chain reaction, immunoassays, etc.) for certain assay steps.

Figure 21C:
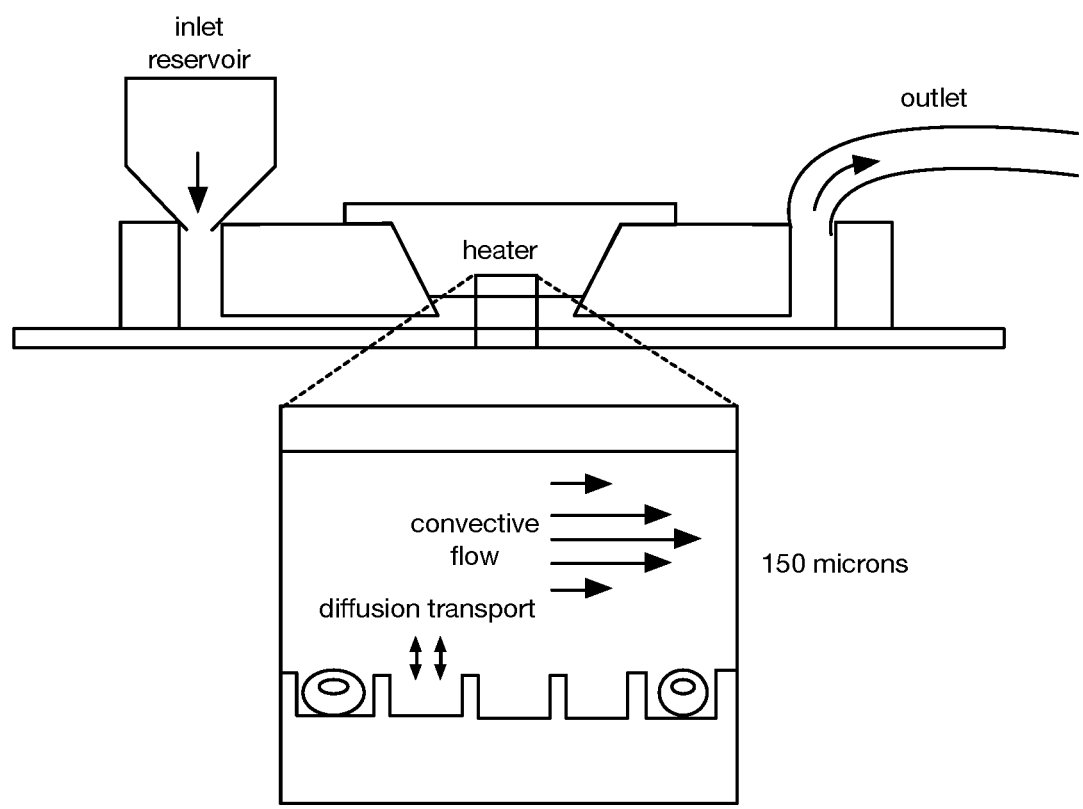

In a specific example, as shown in FIG. 21C, reagent exchanges can be delivered into the set of wells through the use of the manifold system. As shown in FIG. 21C, a heating plate (e.g., an aluminum heater cap with a defined geometry) can be coupled within the recess of the fluid delivery module, wherein the heating plate is clamped down and a thin gasket layer provides a seal between the top surface of the fluid layer defined within the recess, and the flange of the heating plate. In the specific example, an inlet reservoir funnel is placed on the inlet port and an outlet tubing played on the outlet port of the manifold. By placing reagents in the inlet reservoir, flow is established in the gap between the aluminum heater and the nanowell structures by convective flow created by the hydrostatic pressure of reagents in the inlet funnel.

In more detail, the openings of the set of well are very small compared to the cavity (i.e., fluid layer) where convective reagent flow is established. Reagents are transported from the fluid layer into the set of wells by diffusive transport. The times required for diffusive across the nanowell (30 microns deep) can be estimated using the formula, Diffusion Time~(Diffusion Length)$^2$/Diffusivity. A small molecule, such as PCR primer (Diffusivity $10^{-6}$ cm$^2$/s) would take approximately 9 seconds to diffuse across the nanowell. Taq Polymerase with diffusivity of approx. $4.7 \times 10^{-7}$ cm$^2$/s would need about 19 seconds to diffuse across the nanowell. So, in order to deliver "all-in-one" PCR reagents into the nanowell, reagents are convectively transported into the macro-cavity and the sufficient time provided (around 2-3 minutes) for the reagents to diffuse into the nanowells.

As such, the system 100 can further comprise a heating plate coupled to the plate of the fluid delivery module within the recessed region, the heating plate at least partially defining the fluid layer through which a convective flow provided by the heating plate can flow in the second direction parallel to the broad surface, wherein, with the heating plate, the system is operable in a diffusion mode that provides diffusion transport between the convective flow and the set of wells.

The system 100 can additionally include an imaging subsystem 195 that functions to image the contents of the set of wells, and can further function to distinguish target objects (e.g., CTCs, labeled cells, microspheres) captured in the set of wells from other cells or objects in the sample introduced into the system 100. The imaging subsystem preferably includes a fluorescence microscope, but can additionally or alternatively include any suitable imaging mechanism (e.g., an optical microscope, a CCD camera, a photo-diode array, etc.). The fluorescence microscope is preferably operable (e.g., in an identification mode, a detection mode, etc.) to detect a fluorescence signal emitted from a target object one or more of the set of wells, and thereby identify that the well(s) contain(s) a target object. In a specific example, the imaging system (e.g., fluorescence imaging system) can be operable in a mode for providing real-time or near real-time fluorescence imaging of samples processed according to an assay. The imaging subsystem is preferably positioned beneath the substrate and oriented to image the contents of the set of wells through the transparent (or translucent) material of the substrate; alternatively, the imaging subsystem can be positioned above the substrate and oriented to image the contents of the set of wells unobstructed by the material of the substrate itself. However, the imaging subsystem can be otherwise positioned in any suitable manner.

The system 100 can additionally include a flow control subsystem 199 configured to control fluid and/or sample flow through the system 100, as well as reagent flow or the flow of any other suitable fluid through the system. The flow control subsystem is preferably operable in a flow mode, in which the flow control system applies a pressure gradient between the inlet and outlet of the fluid delivery module. The pressure gradient can be a positive pressure gradient (as defined between the inlet and outlet) or a negative pressure gradient, and it may be applied continuously, periodically, asynchronously, in a reciprocating fashion (e.g., between positive and negative), or in any other suitable manner.

1.7 System—Specific Examples

In a first specific example, as shown in FIG. 5, the system 100' includes a set of wells 112' of 250,000 wells arranged in a rectangular packed array, wherein each well 113' is coupled to every adjacent well by a fluid channel formed at the overlap between adjacent wells. In the first specific example, each well in the set of wells 112' has a diameter of 25 microns (e.g., a circumscribed diameter) and a depth of 25 microns, as defined between the base surface 120 and the open surface 130 of each well 113'. The set of wells 112' of the first specific example can receive a sample volume from 0.1 to 10 milliliters in volume; however, other variations of the first specific example can receive any other suitable sample volume. In the first specific example, every fluid channel 141' of a set of fluid channels 140' for each well 113' has a width of 5 microns, in order to enable cell/cell cluster retention, while allowing fluid exchange. In the first specific example, the substrate 105' is coupled between a first plate 171 and a second plate 172, with an absorbant layer 173 situated between the first plate 171 and the substrate 105'. The absorbant layer has a rectangular opening 177 aligned with a rectangular recess 174 of the first plate 171, in order to facilitate fluid flow from a reservoir formed by the recess 174 through the opening 177. Other variations of the first specific example can, however, include any other suitable elements that facilitate cell/cell cluster capture, retention, processing, sorting, and/or analysis in any other suitable manner.

In a second specific example, as shown in FIG. 10, the system 100" includes a set of wells 112" of 414 wells 113" arranged in series, wherein each well 113" (aside from an initial well and a terminal well) is coupled to two adjacent wells in series by fluid channels 141" defined at regions between adjacent wells. In the second specific example, the initial well and the terminal well are each only coupled to one adjacent well in the set of wells 112 by way of fluid channels 141". In the second specific example, the set of wells 112 is arranged in a boustrophedonic pattern, but variations of the second specific example can include arrangement of the set of wells 112 in any other suitable manner (e.g., serpentine pattern, spiral pattern, linear pattern, curvilinear pattern, etc.). In the second specific example, each well in the set of wells 112" has a diameter of 1.1 millimeters (e.g., a circumscribed diameter) and a depth of 1 millimeter, as defined between the base surface 120 and the open surface 130 of each well 113", in order to define an approximately 1 milliliter volume capacity for each well. In the second specific example, every fluid channel 141" of a set of fluid channels 140" for each well 113" has a cross section of 250 microns×250 microns, and is configured proximal the open surfaces 130" of the set of wells 112, in order to enable cell/cell cluster retention, while allowing fluid exchange. Furthermore, in the second specific example, a well 113" is spaced from an adjacent well in the set of wells 112" by a spacing of 2 millimeters. In the second specific example, the substrate 105" is coupled between a first encapsulation layer 191 and a second encapsulation layer 192, each comprising an optically clear laminate, and wherein the second encapsulation layer 192" forms the base surfaces 120 of the set of wells 112. Upon delivery of an encapsulation matrix 199 into the set of wells 112" and transitioning of the encapsulation matrix 199 to a set state, the second encapsulation layer 192 of the encapsulation module 190 is removed to allow passive diffusion through the encapsulation matrix 199 and to encapsulated contents of the set of wells 112. Other variations of the first specific example can, however, include any other suitable elements that facilitate cell/cell cluster capture, retention, processing, sorting, and/or analysis in any other suitable manner.

Additionally or alternatively, the system 100 can include any other suitable element that facilitates cell processing and/or analysis. For instance, the system 100 can include optical elements (e.g., embedded within the substrate 105, coupled to the substrate 105) that function to facilitate imaging. The optical elements function to adjust incoming light, preferably to facilitate imaging. The optical elements can function to bend, reflect, collimate, focus, reject, or otherwise adjust the incoming light. The optical elements are preferably defined within the substrate 105, but can alternatively be defined by any other suitable component of the system 100. Optical elements can include any one or more of: light reflectors disposed within the substrate thickness adjacent the array(s) 110 defined on a surface of the substrate 105 opposite that defining the set of wells 112, microlenses defined on a broad surface of the substrate 105 proximal that defining the set of wells 112, light collimators, light polarizers, interference filters, light reflectors (e.g., 90° illumination elements), elements that minimize excitation rays from going into path of collected fluorescence emission light, diffraction filters, light diffusers, and any other suitable optical element. The system 100 can additionally or alternatively include well affinity mechanisms that function to attract a cell of interest 10 towards a well 113. Well affinity mechanisms can include electric field traps, affinity moieties (e.g., coated to a well surface), features (e.g., microfluidic features) that direct flow into an element, or any other suitable pore affinity mechanism. The system 100 can, however, include any other suitable element(s).

Variations of the system 100 can be operable to facilitate assays in a manner analogous to the methods described in U.S. application Ser. No. 15/333,420 entitled "Cell Capture System and Method of Use" and filed 25 Oct. 2016, U.S. application Ser. No. 14/863,191 entitled "System and Method for Capturing and Analyzing Cells" and filed 23 Sep. 2015, and U.S. application Ser. No. 14/289,155 entitled "System and Method for Isolating and Analyzing Cells" and filed 28 May 2014, which are each incorporated in their entirety by this reference. The system is additionally or alternatively operable for a variety of on-chip (e.g., in situ at the substrate) analyses and assays, including: on-chip immunochemistry, on-chip DNA and/or mRNA FISH, on-chip mRNA and/or DNA PCR, on-chip isothermal amplification, on-chip live cell assays, on-chip cell culture, and other similar assays.

In a specific example, the system may be operated according to the following procedure: a 4 milliliter whole blood sample is partially fixed with an equal volume of 0.4% PFA for 10 minutes; the sample is enriched for cancer cells and washed with PBS; the cells, comprising approximately 85% cancer cells and approximately 20,000 whole blood cells are backflowed with 1 milliliter PBS to generate a backflow solution containing the cells; the backflow solution is flowed over the set of wells 112 of the system 100 and the cells are captured by the wells; an immunostaining reagent is flowed by way of the fluid delivery module to each of the wells of the set of wells; cancer cells are identified using a fluorescence microscope which detects a fluorescence signal emitted by any cells which are successfully tagged by the immunostaining reagent; identified cells are extracted from their corresponding wells using the cell removal module of the system (e.g., a capillary tube on a three-axis traversing stage) and transferred to a PCR tube, where the single cell genome is amplified; the amplified single cell genome is packed for downstream processing (e.g., whole genome sequencing, targeted sequencing, etc.).

Additionally, as a person skilled in the field of cell sorting will recognize from the previous detailed description and from the figures and claims, modifications and changes can be made to the embodiments, variations, examples, and specific applications of the system 100 described above without departing from the scope of the system 100.

2. Method

Figure 12:
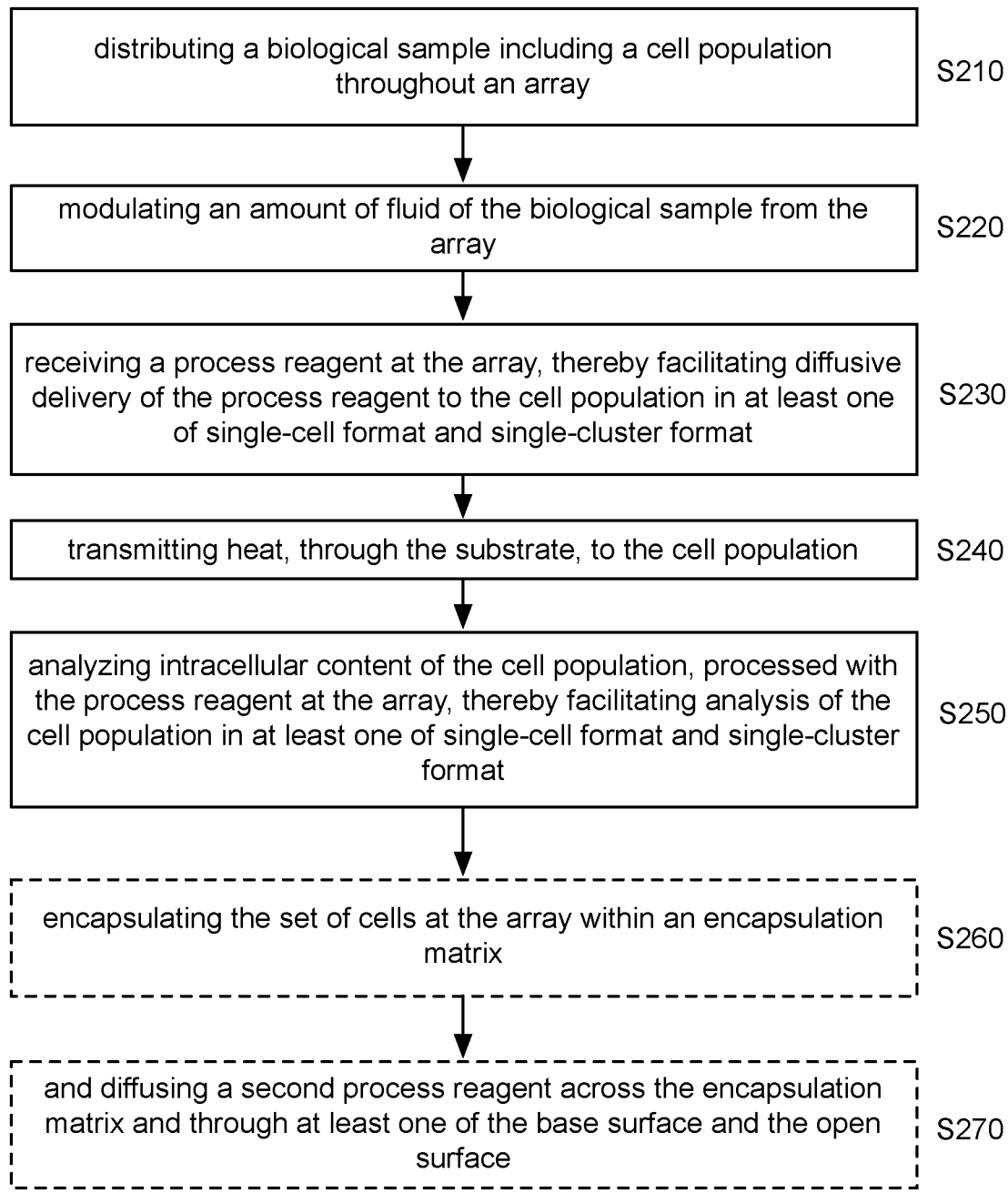
FIG. 12 depicts a schematic representations of an embodiment of a method for isolating and analyzing cells.

As shown in FIG. 12, a method 200 for isolating and analyzing a set of cells comprises: distributing a biological sample including a cell population throughout an array comprising a set of wells defined at the broad surface of a substrate, each well of the set of wells including a base surface, an open surface directly opposing the base surface, defined at the broad surface of the substrate, and configured to retain one of a single cell and a single cluster of cells of the cell population, and a set of channels that fluidly couple each well to at least one adjacent well in the set of wells S210; modulating an amount of fluid of the biological sample from the array S220; receiving a process reagent at the array, thereby facilitating diffusive delivery of the process reagent to the cell population in at least one of single-cell format and single-cluster format S230; transmitting heat, through the substrate, to the cell population S240; and analyzing intracellular content of the cell population, processed with the process reagent at the array, thereby facilitating analysis of the cell population in at least one of single-cell format and single-cluster format S250. The method 200 can additionally or alternatively include any one or more of: encapsulating the set of cells at the array within an encapsulation matrix S260; and diffusing a second process reagent across the encapsulation matrix and through at least one of the base surface and the open surface S270.

The method 200 functions to enable isolation, capture, and retention of cells, more preferably cells in single-cell format and/or single-cluster format, at known, addressable locations, and further to facilitate performance of multiple single-cell/single cluster assays that can be performed on individual cells or cell clusters (e.g., rare cells in a biological sample). The method 200 is preferably implemented at least in part using the system 100 described in Section 1 above; however the method 200 can additionally or alternatively be implemented using any other suitable system 100 for cell capture and analysis. In some embodiments, the method 200 can be used to capture and facilitate analyses of circulating tumor cells (CTCs) and subpopulations of CTCs, such as circulating stem cells (CSCs), but can additionally or alternatively be used to capture any other suitable cell of possible interest for processing and analysis.

Block S210 recites: distributing a biological sample including a cell population throughout an array comprising a set of wells defined at the broad surface of a substrate, each well of the set of wells including a base surface, an open surface directly opposing the base surface, defined at the broad surface of the substrate, and configured to retain one of a single cell and a single cluster of cells of the cell population, and a set of channels that fluidly couple each well to at least one adjacent well in the set of wells. Block S210 functions to receive a biological sample including target cells of interest at an embodiment of the system 100 described in Section 1 above, and to facilitate distribution of the target cells into wells of the system 100 in at least one of single-cell format and single-cluster format. However, Block S210 can alternatively include receiving a biological sample at any other suitable system configured to capture cells in at least one of single-cell format and single-cluster format. In variations of Block S210, the biological sample can be received directly at a variation of the array (e.g., by pipetting, by fluid delivery through a fluid channel coupled to the array), at the array by way of a variation of the first plate of a fluid delivery module (e.g., from a reservoir defined by a recess of the first plate, from a fluid channel coupled to the first plate, from a fluid channel embedded within the first plate and in fluid communication with the array, etc.), and/or in any other suitable manner. Furthermore, in variations of Block S210, the cell population can include a cell population of target cells (e.g., CTCs, CSCs) and/or any other suitable particle of interest.

In variations of Block S210, distributing can include any one or more of: cytospinning the substrate with the biological sample about an axis parallel to the broad surface of the substrate, cytospinning the substrate with the biological sample about an axis perpendicular to the broad surface of the substrate, cytospinning the substrate with the biological sample about an axis oriented at any suitable angle relative to the broad surface of the substrate, smearing the biological sample at the array of the substrate, depositing the biological sample at the array under positive and/or negative pressure (e.g., by way of a pumping mechanism), incubating the biological sample at the array for a period of time, and in any other suitable manner of sample deposition and distribution. Furthermore, in applications of Block S210 including cytospinning, an axis of rotation can be offset from any suitable reference point of the substrate, in any suitable manner. In one specific application, as shown in FIG. 8, Block S210 includes rotating an assembly comprising a first plate coupled to a second plate and with the substrate and an absorbant layer between the first plate and the second plate, about an axis of rotation parallel to and offset from the broad surface of the substrate, such that the normal defined by the broad surface of the substrate passes through the axis of rotation. As such in the specific example, during rotation of the assembly, fluid within a reservoir formed by a recess of the first plate can be pushed toward the wells of the array by centripetal force (e.g., to capture cells at the wells), while excess fluid can flow into the absorbant layer. In the specific application, the assembly is rotated at an angular velocity from 500-2000 revolutions per minute; however, other variations of the specific application can include rotation of any other suitable assembly at any other suitable angular velocity. Furthermore, in variations of the specific application, the assembly can be rotated about any other suitable axis, and/or capturing of cells at the array can be performed in any other suitable manner.

Block S220 recites: modulating an amount of fluid of the biological sample at the array, which functions to increase, decrease, or maintain an amount of fluid, from the biological sample, at the array, thereby facilitating capture of cells at the array in at least one of single-cell format and single-cluster format. Block S220 preferably includes reducing an amount of fluid at the array; however, Block S220 can additionally or alternatively include increasing or maintaining an amount of fluid at the array. In variations, Block S220 can include modulating the amount of fluid by any one or more of: applying negative and/or positive pressure at the array (e.g., at a pump coupled to the system 100), using capillary soaking, by evaporation (e.g., using a heating element of the system, by passive evaporation), and any other means of modulating an amount of fluid at the array. In one variation, Block S220 can include providing an absorbant layer at the array, configured to absorb excess fluid at the array by capillary soaking. In a specific example of this variation, the absorbant layer can include an opening aligned with the array, as described in Section 1 above, wherein cytospinning of a substrate including the array simultaneously forces cells into the set of wells of the array in at least one of single-cell format and single-cluster format and facilitates flow of excess fluid into the absorbant layer. As such, in some variations, Block S220 can be performed simultaneously with Block S210 (e.g., in cytospinning applications), or can alternatively be performed prior to or after Block S210.

Block S230 recites: receiving a process reagent at the array, thereby facilitating diffusive delivery of the process reagent to the cell population in at least one of single-cell format and single-cluster format. The process reagent can include any one or more of: a lysing reagent, a fixing reagent, a permeabilization reagent, a stain, a reagent for immunochemistry, a reagent for an in-situ hybridization assay (e.g., a fluorescence in-situ hybridization assay, FISH) for nucleic acids (e.g., DNA, RNA, mRNA, etc.), a reagent for polymerase chain reaction (PCR), a culture reagent (e.g., media) for cell maintenance and/or subsequent harvesting from the array, and any other suitable reagent. In variations, the process reagent(s) can be delivered to and distributed across the array in a manner similar to that of distributing the biological sample at the array in variations of Block S210. Additionally or alternatively, the amount(s) of the process reagent(s) at the array can be modulated in a manner similar to that of modulating fluid as in variations of Block S220. However, receiving the process reagent(s) and/or modulating the amount(s) of the process reagent(s) can additionally or alternatively be performed in any other suitable manner.

Block S240 recites: transmitting heat, through the substrate, to the cell population captured at the array, which functions to provide controlled incubation and/or thermocycling of the cell population with the process reagent(s) received in variations of Block S230. Block S240 preferably includes providing uniform heating at each well of the set of wells of the array; however, Block S240 can alternatively include providing heat non-uniformly across the array (e.g., providing heat with a gradient to examine effects of different heating parameters on the cell population). In variations, Block S240 can include contacting the substrate with at least one heating element, adjusting an environmental temperature of the substrate, or transmitting heat throughout the substrate by way of heating elements coupled to or embedded within the substrate. However, transmitting heat through the substrate can additionally or alternatively be performed in any other suitable manner. Transmitting heat thus includes incubating the substrate, with the cell population and a process reagent for a desired amount of time at a desired temperature, according to parameters suited for the process reagent(s) provided in Block S230. As such, transmitting heat can facilitate one or more of: lysing the cell population, fixing the cell population, permeabilizing the cell population, staining the cell population, performing immunochemistry for the cell population, binding a probe to intracellular nucleic acid content of the cell population, as in an in-situ hybridization assay (e.g., a fluorescence in-situ hybridization assay, FISH), performing polymerase chain reaction for nucleic acid content of the cell population, culturing the cell population, and any other suitable application.

In variations of the method 200, Blocks S220, S230, and/or S240 can be performed with any suitable number of repetitions, according to protocols for processing the cell population according to different assays. For instance, removing excess fluid can be performed prior to and/or after heating the substrate, in order to remove excess process reagent(s) from the array after they are no longer needed. Furthermore, Blocks S220, S230, and/or S240 can be performed in any suitable order or simultaneously, according to protocols for processing the cell population according to different assays.

Block S250 recites: analyzing intracellular content of the cell population, processed with the process reagent at the array, thereby facilitating analysis of the cell population in at least one of single-cell format and single-cluster format. In variations, Block S250 can include any one or more of: harvesting contents of the set of wells (e.g., cells, intracellular content), culturing cells captured at the set of wells, detecting biomarkers exhibited by the cell population (e.g., using fluorescent detection), performing a quantitative analysis (e.g., a quantitative analysis of mRNA expression), characterizing a cell phenotype (e.g., a cancer cell phenotype) based upon biomarker expression, providing a recommended therapy based upon characterization of a cell phenotype, performing flow cytometry with captured cells of the cell population, and performing any other suitable analysis. The analyses performed in variations can thus be performed for cells within and/or harvested from the array.

As shown in FIG. 12, the method 200 can additionally or alternatively include Block S260, which recites: encapsulating the set of cells at the array within an encapsulation matrix. Block S230 functions to isolate captured cells of interest at the set of wells, in order to facilitate further processing and analysis of the set of cells in at least one of single-cell format and single-cluster format. The encapsulation matrix preferably isolates a well and its contents within the array, in an embodiment of the system 100 described above; however, the encapsulation matrix can isolate particles in any other manner and/or in any other suitable system. The encapsulation matrix preferably has a flow state and a set state, wherein a photochemical reaction, thermochemical reaction, polymerization reaction and/or any other suitable reaction switches the encapsulation matrix from the flow state to the set state. In the flow state, the encapsulation matrix is preferably substantially viscous, such that the encapsulation matrix does not flow into the pores during introduction into the system 100. In the set state, the encapsulation matrix is preferably a solid or gel that prevents particle egress from the pores (e.g., egress of cells, reagent particles, and large nucleic acid molecules from the pores), and is preferably porous or selectively permeable to permit small molecule, buffer, and reagent (e.g., detergent, enzyme, primer, etc.) penetration therethrough. Furthermore, by changing the constituents of a buffer or reagent and allowing sufficient time for diffusion, specific reagents/buffers can be entered into or eluted out from encapsulated cells. In one variation, the encapsulation matrix is a microporous agarose gel with a low melting point, and in another variation, the encapsulation matrix is a photopolymerizable hydrogel, such as PEG or polyacrylamide with photoinitiator; however, the encapsulation matrix can alternatively be any suitable material with any other suitable polymerization agent.

In relation to the system 100 described in Section 1 above, the encapsulation matrix can isolate contents of the set of wells between at least one of a first encapsulation layer and a second encapsulation layer, such that Block S260 includes delivering the encapsulation matrix into a fluidic network defined between the substrate, the first encapsulation layer, and/or the second encapsulation layer in a flow state prior to setting the encapsulation matrix. As such, variations of Block S260 can include delivering the encapsulation matrix to the array through an opening that provides access to the array (e.g., a fluid port), or in any other suitable manner.

Also shown in FIG. 12, the method 200 can additionally or alternatively include Block S270, which recites: diffusing a second process reagent across the encapsulation matrix S270 and through at least one of the base surface and the open surface of a well of the array. The second process reagent can include any one or more of: a lysing reagent, a fixing reagent, a permeabilization reagent, a stain, a reagent for immunochemistry, a reagent for an in-situ hybridization assay (e.g., a fluorescence in-situ hybridization assay, FISH) for nucleic acids (e.g., DNA, RNA, mRNA, etc.), a reagent for polymerase chain reaction (PCR), a culture reagent (e.g., media) for cell maintenance and/or subsequent harvesting from the array, and any other suitable reagent, as in Block S230. The second process reagent is preferably diffused across the encapsulation matrix, to contents of the set of wells through the base surfaces of the wells of the set of wells, but can additionally or alternatively be diffused across the encapsulation matrix, to contents of the set of wells through the open surfaces of the wells of the set of wells. As such, in relation to the system 100 described in Section 1 above, Block S250 can include removing at least one of the second encapsulation layer and the first encapsulation layer, and providing a reagent at the exposed surface(s) of the substrate to facilitate diffusing of the second process reagent(s) into the wells of the array. Block S250 preferably includes delivering the second process reagent(s) uniformly to each well of the set of wells of the array; however, Block S250 can alternatively include delivering the second process reagent(s) non-uniformly to the set of wells of the array. Furthermore, Block S250 can additionally or alternatively include actively driving the second process reagent(s) across the encapsulation matrix, for instance, by providing pressure (e.g., positive pressure, negative pressure) at the array or by providing centripedal force at the array.

The method 200 can additionally or alternatively include any other suitable steps or blocks that facilitate reception, processing, and/or analysis of the cell population in at least one of single-cell format and single-cluster format.

2. Method—Specific Applications

In a first specific application, the method 200 is configured to facilitate automated FISH analysis of intracellular DNA of a cell population (e.g., from a patient) at an embodiment of the system 100 described in Section 1 above. Furthermore, variations of the first specific application can include performing immunochemistry following performance of the FISH analysis, in order to characterize the cell population. The first specific application can thus facilitate recommendation of therapies target to the patient providing a biological sample including the cell population, in a patient-specific manner. In some examples, the therapies can include Herceptin for Her-2 positive patients, and Xalkori for ALK-positive non-small cell lung cancer patients.

In a second specific application, the method 200 is configured to facilitate automated FISH analysis of intracellular mRNA of a cell population (e.g., from a patient) at an embodiment of the system 100 described in Section 1 above, in order to characterize the cell population. In the second specific example, the FISH analysis includes quantitative analysis of mRNA expression for each cell, including multiplexing of multiple biomarkers (e.g., 6 biomarkers) for each cell using a set of fluorophores provided in a suitable process reagent.

In a third specific application, the method 200 is configured to facilitate FISH analysis of intracellular mRNA of a cell population (e.g., from a patient) at an embodiment of the system 100 described in Section 1 above. Furthermore, variations of the third specific application can include performing immunochemistry in combination with performance of the FISH analysis, in order to characterize the cell population. In an example, SUM159 breast cancer cells, pre-selected for CD44+ and CD24− antibodies, and isolated in at least one of single-cell format and single-cluster format can be analyzed with immunochemistry and FISH assays in the third specific application.

In a fourth specific application, the method 200 is configured to facilitate capture of viable cancer cells at an embodiment of the system 100 described in Section 1 above. In the fourth specific application, the captured cells are then harvested from the array after a period of incubation, for use in applications including drug discovery testing, sequencing of cells (e.g., CTCs), and development of improved cancer cell characterization assays.

The system 100 and method 200 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A system for isolating and analyzing a population of target particles from a biological sample in single-particle format, the system comprising:
   a substrate having a broad surface, wherein the substrate defines an inlet and a set of wells in fluid communication with and downstream of the inlet, the set of wells arranged in a hexagonal close-packed configuration, wherein each well in the set of wells is configured to receive and retain a target particle of the population of target particles and comprises:
   a base surface defined within the substrate,
   an open surface directly opposing the base surface, and
   a well cavity defined by the base surface and the open surface, the well cavity having a longitudinal axis arranged normal to a flow direction from the inlet and across the open surface, and
   wherein the substrate defines the set of wells at a region having a total surface area of at least 144 square millimeters, and wherein the set of wells comprises at least 250,000 individual wells within the total surface area; and
   a cavity configured to provide a boundary of a fluid layer adjacent to the well cavities of the set of wells.

2. The system of claim 1, wherein the well cavity defines a prismatic volume.

3. The system of claim 2, wherein the prismatic volume comprises a hexagonal prismatic volume.

4. The system of claim 1, wherein each well further comprises a set of walls extending between the base surface and the open surface, wherein each wall in the set of walls has a wall thickness that is equal to or less than five microns.

5. The system of claim 4, wherein the set of walls of at least one well defines a hexagonal footprint about the base surface of the at least one well.

6. The system of claim 1, wherein the open surface of at least one well in the set of wells defines a characteristic dimension that is less than 50 microns.

7. The system of claim 1, further comprising a fluid delivery subsystem comprising a manifold configured to interface with the inlet of the substrate and the open surfaces of the set of wells.

8. The system of claim 7, wherein the fluid delivery subsystem further comprises a delivery inlet and an outlet fluidly coupled by and arranged on opposing sides of the fluid layer, and wherein the delivery inlet and the delivery outlet are fluidly coupled to a flow control subsystem operable in a flow mode that applies one of a positive pressure gradient and a negative pressure gradient between the delivery inlet and the delivery outlet.

9. The system of claim 7, wherein the fluid delivery subsystem comprises an upper plate reversibly coupleable to the substrate, wherein the upper plate spans at least a portion of the broad surface of the substrate, and is arranged superior to the set of wells.

10. The system of claim 9, wherein the upper plate comprises a recess facing the broad surface of the substrate and, upon attaching the upper plate to the substrate, the recess and the broad surface cooperatively defining the cavity adjacent to the well cavities of the set of wells.

11. The system of claim 1, further comprising a thermal control subsystem comprising a heating plate abutting the cavity and promoting convective flow in the flow direction, upon heating of the fluid layer during operation.

12. The system of claim 11, wherein the heating plate seals the cavity adjacent to the well cavities of the set of wells.

13. The system of claim 1, wherein the population of target particles comprises a population of viable rare cells, and wherein the system is configured to provide flow through the fluid layer for transmission of captured rare cells, from the set of wells, in a viable state.

14. The system of claim 1, wherein the set of wells comprise a plurality of subsets of wells, wherein the wells in the subset of wells are fluidly connected to one another by a set of fluidic channels.

15. The system of claim 14, wherein each subset of wells includes six peripheral wells arranged about a central well within the plane of the broad surface of the substrate, and wherein each peripheral well is fluidly connected to the central well.

16. A system for isolating and analyzing a population of target particles in single-particle format, the system comprising:
   a substrate having a broad surface, wherein the substrate defines an inlet and a set of wells in fluid communication with and downstream of the inlet, the set of wells arranged in a close-packed configuration,
   wherein each well in the set of wells is configured to receive and retain a target particle of the population of target particles and comprises:

a base surface defined within the substrate, an open surface directly opposing the base surface, and a well cavity defined by the base surface and the open surface, the well cavity having a longitudinal axis arranged normal to a flow direction from the inlet and across the open surface, and wherein the set of wells comprises at least 250,000 individual wells configured to collectively receive from 0.1 to 10 milliliters of fluid; and a cavity configured to provide a boundary of a fluid layer adjacent to the well cavities of the set of wells.

17. The system of claim 16, wherein the well cavity defines a hexagonal prismatic volume.

18. The system of claim 16, wherein the open surface of at least one well in the set of wells defines a characteristic dimension that is less than 50 microns.

19. The system of claim 16, further comprising a fluid delivery subsystem comprising a manifold configured to interface with the inlet of the substrate and the open surfaces of the set of wells, wherein the manifold is configured to seal the cavity of the substrate.

20. The system of claim 16, further comprising a thermal control subsystem comprising a heating plate abutting the cavity and promoting convective flow in the flow direction, upon heating of the fluid layer during operation.

* * * * *